US006770631B1

(12) United States Patent
Cox et al.

(10) Patent No.: US 6,770,631 B1
(45) Date of Patent: Aug. 3, 2004

(54) NON-IDENTICAL GENES AND THEIR APPLICATION IN IMPROVED MOLECULAR ADJUVANTS

(75) Inventors: Vivienne Frances Cox, Royston (GB); Richard Anthony Godwin Smith, Royston (GB); Pamela Jane Elizabeth Rowling, Royston (GB)

(73) Assignee: AdProTech Limited, Essex (GB)

( * ) Notice: Subject to any disclaimer, the term of this patent is extended or adjusted under 35 U.S.C. 154(b) by 0 days.

(21) Appl. No.: 09/582,761

(22) PCT Filed: Dec. 30, 1998

(86) PCT No.: PCT/GB98/03918

§ 371 (c)(1),
(2), (4) Date: Aug. 28, 2000

(87) PCT Pub. No.: WO99/35260

PCT Pub. Date: Jul. 15, 1999

(30) Foreign Application Priority Data

Dec. 31, 1997 (GB) .............................................. 9727512

(51) Int. Cl.[7] .............................................. A61K 48/00
(52) U.S. Cl. ..................... 514/44; 435/91.4; 435/320.1; 435/455
(58) Field of Search ......................... 514/49; 435/320.1, 435/455, 91.4

(56) References Cited

U.S. PATENT DOCUMENTS

| | | | | |
|---|---|---|---|---|
| 5,049,658 | A | * | 9/1991 | Kimizuka et al. |
| 5,641,648 | A | * | 6/1997 | Ferrari et al. |
| 5,767,260 | A | * | 6/1998 | Whitlow et al. |
| 5,861,285 | A | * | 1/1999 | Matsunaga |
| 6,018,030 | A | * | 1/2000 | Ferrari et al. |
| 6,265,562 | B1 | * | 7/2001 | Eilers et al. |

FOREIGN PATENT DOCUMENTS

| | | |
|---|---|---|
| WO | WO88/03533 | 5/1988 |
| WO | WO93/12257 | 6/1993 |
| WO | WO96/17625 | 6/1996 |

OTHER PUBLICATIONS

McCluskie et al. Route and method of delivery of DNA vaccine influence immune responses in mice and non–human primates 1999.*

Verma et al. Gene therapy promises, problems and prospects pp. 239–242 vol. 389 1997.*

Anderson Human gene therapy pp.25–30 vol. 392 1998.*

Journal of Immunological Methods 178: 201–209 (1995).

Nucleic Acids Research 18(12): 3587–3596.

* cited by examiner

*Primary Examiner*—Dave Trong Nguyen
(74) *Attorney, Agent, or Firm*—Heller Ehrman White & McAuliffe

(57) ABSTRACT

The invention provides a linear concatamer of at least two non-identical DNA sequences which, by virtue of third base redundancy of the genetic code of the codons, each encode the same polypeptide of at least 30 amino acids; wherein the concatamer comprises or consists of a nucleic acid sequence which codes for an oligomer of said polypeptides in a continuous reading frame. A single invariant cysteine codon may be added to one DNA sequence to encode a polypeptide derivative with a unique unpaired cysteine. The concatamer may be fused to one or more sequences encoding one or more antigens. The DNA sequences in the concatamer may encode the compliment C3 fragment C3d or an analogue thereof. The invention also provides an expression vector comprising the concatamer nucleic acid sequence and regulatory or other sequences for expression of any oligomeric polypeptide encoded thereby, as well as a host cell comprising the expression vector. The invention can also provide a method of including a immune response to an antigen in the human or animal by administering a concatamer or administering a vector. Thus the invention can provide a pharmaceutical composition in the form of a DNA vaccine.

16 Claims, No Drawings

NON-IDENTICAL GENES AND THEIR APPLICATION IN IMPROVED MOLECULAR ADJUVANTS

This application is a 371 of PCT/GB98/03918, filed Dec. 30, 1998, which is hereby incorporated by reference.

This invention relates to novel genetic constructs designed to permit expression or synthesis multidomain proteins containing extended repetitive sequences, particularly those useful for the creation of molecular adjuvants and immunogens.

The complement system consists of a set of serum proteins that are important in the response of the immune system to foreign antigens. The complement system becomes activated when its primary components are cleaved and the products, alone or with other proteins, activate additional complement proteins resulting in a proteolytic cascade. Activation of the complement system leads to a variety of responses including increased vascular permeability, chemotaxis of phagocytic cells, activation of inflammatory cells, opsonisation of foreign particles, direct killing of cells and tissue damage. Activation of the complement system may be triggered by antigen-antibody complexes (the classical pathway) or a normal slow activation may be amplified in the presence of cell walls of invading organisms such as bacteria and viruses (the alternative pathway). The complement system interacts with the cellular immune system through a specific pathway involving C3, a protein central to both classical and alternative pathways. The proteolytic activation of C3 gives rise to a large fragment (C3b and exposes a chemically reactive internal thiolester linkage which can react covalently with external nucleophiles such at the cell surface proteins of invading organisms or foreign cells. As a result, the potential antigen is 'tagged' with C3b and remains attached to that protein as it undergoes further proteolysis to iC3b and C3d,g. The latter fragments are, respectively, ligands for the complement receptors CR3 and CR2. Thus the labelling of antigen by C3b can result in a targeting mechanism for cells of the immune system bearing these receptors.

That such targeting is important for augmentation of the immune response is first shown by experiments in which mice were depleted of circulating C3 and then challenged with an antigen (sheep erythrocytes). Removal of C3 reduced the antibody response to this antigen. (M. B. Pepys, J.Exp.Med, 140, 126–145, 1974). The role of C3 was confirmed by studies in animals genetically deficient in either C3 or the upstream components of the complement cascade which generate C3b, i.e. C2 and C4, (J. M. Ahearn & D. T. Fearon, Adv.Immunol. 46, 183–219, 1989). More recently, it has been shown that linear conjugation of a model antigen with more than two copies of the murine C3d fragment sequence resulted in a very large (1000–10000-fold) increase in antibody response in mice compared with unmodified antigen controls (P. W. Deropsey et al, Science, 271: 348–350, 1996; WO96/17625, PCT/GB95/02851). The increase could be produced without the use of a conventional adjuvants such as Freund's complete adjuvant. The mechanism of this remarkable effect was demonstrated to be high-affinity binding of the multivalent C3d construct to CR2 on B-cells, followed by co-ligation of CR2 with another B-cell membrane protein, CD19 and with membrane-bound immunoglobulin to generate a signal to the B-cell nucleus.

In these experiments, the unmodified antigen control and linear fusions with one or two C3d domains were prepared by transfection of the appropriate coding plasmids into L cells followed by the selection of high-expressing clones. The most immunogenic construct that with three C3d units, had to be expressed transiently in COS cells and this procedure gave a very poor yield of the fusion protein. In part, the low yield could be attributed to the generation of species containing the antigen but with lower molecular weights, corresponding to fewer than three C3d units. It was unclear from the published work of Dempsey et al whether the latter molecules originated by proteolysis of the three-C3d construct or whether they were due to a recombination event in vivo.

Using another expression system but the same C3d constructs as Dempsey et al. we have now obtained evidence that the generation of molecules with <3 C3d units from DNA encoding 3× C3d repeats is due to loss of one or more C3d units by homologous recombination and not due to post-translational processing (see below). This observation has also identified an efficient system for the expression of the C3d monomer.

It is known generally that the production of high molecular weight polypeptides containing multiple repeating sequences is difficult because of the tendency of repeated DNA sequences to undergo rearrangement during replication. Some of the limitations on internal repetitiveness in plasmids have been discussed by Gupta (Bio/Technology 1. 602–609, 1983). Ferrari et al (U.S. Pat. No. 5,641,648) have described methods for expression of repetitive sequences using synthetic genes constructed from monomeric units which are concatenated by ligation. DNA sequences encoding the same repeated amino acid sequence but differing in nucleotide sequence either within or between monomers were constructed by exploiting the redundancy of the genetic code. The resulting lack of precise repetitiveness at the nucleotide level reduced homologous recombination to the point where the repeated oligopeptide sequence could be expressed. The work of Ferrari et al was restricted to relatively short repeating units of 4 to 30 codons (amino-acids) repeated a large number of times (typically ~30-fold).

The present invention describes a general method for introducing variability into entire genes or fragments of genes, particularly those encoding autonomously folding protein domains or motifs of>30 amino acids, in such a way that different DNA units encoding identical or near-identical amino acid sequences can be concatenated and expressed to give domain oligomers.

The invention comprises the following elements:

1. The construction of novel synthetic DNA sequences encoding an autonomously folding polypeptide domain and using in these DNA sequences the maximum third-base redundancy in each codon permitted by the genetic code which is consistent with a continuous reading frame and retention of the amino acid sequence. These mixtures of DNA molecules are termed 'Fuzzy Gazes'.
2. Using these libraries to isolate or design concatamers in which the DNA repeats differ from each other in the third base positions. These concatamers may be made with or without in-frame coding regions for other proteins.
3. Placing these sequences either as mixed populations or single characterised concatamers into a suitable expression vector and expressing the population in a recombinant host cell.
4. The use of assays able to detect the presence of repeated-domain expressed protein products. Host cell clones are screened for those capable of producing useful levels of functionally active polypeptide concatamers/fusion proteins.
5. Where necessary, characterising one or more unique DNA sequences derived from these clones and encoding the expressed product.

6. Using the unique chemical reactivity of single cysteine residues in expressed proteins to assemble protein derivatives with multiple copies of a domain by post-translational chemical modification combined with concatamerisation at the DNA level.

In specific embodiments of the invention, the autonomously folding repeated protein domain is a ligand for one or mare cell surface receptors involved in the regulation of the immune system. One such example is human or murine C3d or C3d,g polypeptide sequence or another peptide ligand of CR2 (CD21) or CD 19.

In a second embodiment the additional domain may be an immunogen, particularly an antigenic protein or region of a protein. Examples of polypeptide immunogens include but are not restricted to: the Hepatitis B surface antigen, meningococcal surface proteins, proteins expressed at various stages of the life cycle of the malaria parasite, the glucan-binding region of streptococcal glucosyltransferases, the haemagglutinin (H) and neuraminidase (N) proteins of influenza virus strains and the D-repeat regions of the fibronectin binding proteins of staphylococci.

Optionally, an antigen oligomer may be fused to a C3d oligomer, either or both component being expressed from fuzzy or partially fuzzy genes.

In a third embodiment, the expressed oligomeric protein may be derivatised to facilitate post-translational linkage to an antigen or other protein. Preferably, such derivatisation is effected by engineering a reactive residue such as a free cysteine or a thiolester group at a unique site in the oligomer, preferably at the C- or N-terminus.

In a further aspect, the invention also provides for expression of closely related polypeptides in a single linear molecule by the ligation of fuzzy DNA sequences encoding near-identical amino acid sequences. In this context, near-identical signifies sequences differing by at least one amino acid but not in more 10% of the total number of amino acids. Examples of such constructs include but are not restricted to genes encoding several variations of a protein or antigen and concatenated immunoglobulin single-chain $F_v$ fragments with a similar overall architecture but containing small variations in the complementarity-determining regions so that they recognise different antigens.

Another embodiment of the invention utilises the novel DNA sequences identified by the selection process noted above as components of expression vectors for genetic (or DNA) immunisation. In this application, the preferred DNA sequences for expression in a given cell type (such as a human cell line) are identified by screening cells of that type transfected with a fuzzy or partially fuzzy DNA pool (within a suitable vector) for expression of the desired construct. This application may be further extended by chemically linking the expressed, derivatised C3d (or other protein) oligomers to DNA-binding molecules such as cationic lipids, lipopeptides or liposomes so that vectors for DNA immunisation may be targeted to particular cell types. Thus, for example, a C3d trimer linked to a liposome containing DNA encoding a $(C3d)_3$-antigen fusion could be targeted to dendritic cells. Expression of the construct by the dendritic cells could then present a targeted antigen locally to further B-lineage cells thus achieving a dual-level selectivity.

The above steps involve the following general processes:

The invention provides a process for preparing oligomeric polypeptides according to the invention which process comprises expressing DNA encoding said polypeptide in a recombinant host cell and recovering the product. That process may comprise the steps of :

(i) preparing a variable (replicable expression vector capable, in a host cell, of expressing a DNA polymer comprising a nucleotide sequence that encodes said polypeptide;

ii) transforming a host cell with said vector;

iii) culturing said transformed host cell under conditions permitting expression of said DNA polymer to produce said polypeptide; and iv) recovering said polypeptide in an active form.

The variant DNA polymers comprising a nucleotide sequence that encodes the polypeptide also forms part of the invention.

The process of the invention may be performed using conventional recombinant techniques such as described in Sambrook et al., Molecular Cloning: A laboratory manual 2nd Edition. Cold Spring Harbor Laboratory Press (1989) and DNA Cloning vols I, II and III (D. M. Glover ed., IRL Press Ltd).

The invention also provides a process for preparing the DNA polymer by the condensation of appropriate mono-, di- or oligomeric nucleotide units.

The preparation may be carried out chemically, enzymatically, or by a combination of the two methods, in vitro or in vivo as appropriate. Thus, the DNA polymer may be prepared by the enzymatic ligation of appropriate DNA fragments, by conventional methods such as those described by D. M. Roberts et al., in Biochemistry 1985, 24, 5090–5098.

The DNA fragments may be obtained by digestion of DNA containing the required sequences of nucleotides with appropriate restriction enzymes, by chemical synthesis, by enzymatic polymerisation, or by a combination of these methods.

Digestion with restriction enzymes may be performed in an appropriate buffer at a temperature of 20°–70° C., generally in a volume of 50 $\mu$l or less with 0.1–10 $\mu$g DNA. Enzymatic polymerisation of DNA may be carried out in vitro using a DNA polymerase such as DNA polymerase 1 (Klenow fragment) in an appropriate buffer containing the nucleoside triphosphates dATP, dCTP, dGTP and dTTP as required at a temperature of 10–37° C., generally in a volume of 50 $\mu$l or less Enzymatic ligation of DNA fragments may be carried out using a DNA ligase such as T4 DNA ligase in an appropriate buffer at a temperature of 4° C. to 3° C., generally in a volume of 50 $\mu$l or less.

The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie, Weinheim (1982), or in other scientific publications, for example M. J. Gait, H. W. D. Matthes M. Singh, B. S. Sproat and R. C. Titmas, Nucleic Acids Research, 1982, 10, 6243; B. S. Sproat and W. Bannwarth, Tetrahedron Letters, 1983, 24, 5771; M. D. Matteucci and M. H. Caruthers, Tetrahedron Letters, 1980, 21, 719; M. D. Matteucci and M. H. Caruthers, Journal of the American Chemical Society, 1981, 103, 3185; S. P. Adams et al., Journal of the American Chemical Society, 1983, 105, 661; N. D. Sinha, J. Biernat, J. McMannus and H. Koester. Nucleic Acids Research, 1984, 12, 4539; and H. W. D. Matthes et al., EMBO Journal., 1984, 3, 801. Preferably an automated DNA synthesiser (for example, Applied Biosystems 381A Synthesiser) is employed.

The DNA polymer is preferably prepared by ligating two or more DNA molecules which together comprise a DNA sequence encoding the polypeptide. The DNA molecules may be obtained by the digestion with suitable restriction enzymes of vectors carrying the required coding sequences.

The precise structure of the DNA molecules and the way in which they are obtained depends upon the structure of the desired product. The DNA molecule encoding the polypeptide may be constructed using a variety of methods including chemical synthesis of DNA oligonucleotides, enzymatic polymerisation, restriction enzyme digestion and ligation. The design of a suitable strategy for the construction of the DNA molecule coding for the polypeptide is a routine matter for the skilled worker in the art.

The systematic variation of third-base usage is described in more detail below (Example 3, Table 1) and additional consideration may be given to the avoidance of rarely used codons of the particular host cell.

The expression of the DNA polymer encoding the polypeptide in a recombinant host cell may be carried out by means of a replicable expression vector capable, in the host cell of expressing the DNA polymer. The expression vector is novel ad also forms part of the invention.

The replicable expression vector may be prepared in accordance with the invention, by cleaving a vector compatible with the host cell to provide a linear DNA segment having an intact replicon, and combining said linear segment with one or more DNA molecules which, together with said linear segment, encode the polypeptide, under ligating conditions.

The ligation of the linear segment and more than one DNA molecule may be carried out simultaneously or sequentially as desired. Thus, the DNA polymer may be preformed or formed during the construction of the vector, as desired. The choice of vector will be determined in part by the host cell, which may be prokaryotic, such as $E.$ $coli$, mammalian, such as mouse C127, mouse myeloma. Chinese hamster ovary, or other eukaryotic (fungi e.g. filamentous fungi or unicellular yeast or an insect cell such as Drosophila or Spodopiera). The host cell may also be in a transgenic animal. Suitable vectors include plasmids, bacteriophages, cosmids and recombinant viruses derived from, for example, baculoviruses or vaccinia.

The DNA polymer may be assembled into vectors designed for isolation of stable transformed mammalian cell lines expressing the fragment e.g. bovine papillomavirus vectors in mouse C127 cells, or amplified vectors in Chinese hamster ovary cells (DNA Cloning Vol. II D. M. Glover ed. IRL Press 1985; Kaufman R. J. et al., Molecular and Cellular Biology 5, 1750–1759, 1985; Pavlakis G. N. and Hamer, D. H. Proceedings of the National Academy of Sciences (USA) 80, 397–401, 1983; Goeddel, D. V. et al. European Patent Application No. 0093619, 1983).

The preparation of the replicable expression vector may be carried out conventionally with appropriate enzymes for restriction, polymerisation and ligation of the DNA, by procedures described in, for example, Sambrook et al., cited above. Polymerisation and ligation may be performed as described above for the preparation of the DNA polymer. Digestion with restriction enzymes may be performed in an appropriate buffer at a temperature of 20°–70° C., generally in a volume of 50µl or less with 0.1–10 µg DNA.

The recombinant host cell is prepared, in accordance with the invention, by transforming a host cell with a replicable expression vector of the invention under transforming conditions. Suitable transforming conditions are conventional and are described in, for example, Sambrook et al., cited above, or "DNA Cloning" Vol. II, D. M. Glover ed., IRL Press Ltd, 1985.

The choice of transforming conditions is determined by the host cell. Thus, a bacterial host such as $E.$ $coli$, may be treated with a solution of $CaCl_2$ (Cohen et al., Proc. Nat. Acad. Sci., 1973, 69, 2110) or with a solution comprising a mixture of RbCl, $MnCl_2$, potassium acetate and glycerol, and then with 3-[N-morpholino]-propane-sulphonic acid, RbCl and glycerol or by electroporation as for example described by Bio-Rad Laboratories, Richmond, Calif., USA, manufacturers of an electroporator. Eukaryotic cells in culture may be transformed by calcium co-precipitation of the vector DNA onto the cells or by using cationic liposomes.

The invention also extends to a host cell transformed with a variable replicable expression vector of the invention.

Culturing the transformed host cell under conditions permitting expression of the DNA polymer is carried out conventionally, as described in, for example, Sambrook et al., and "DNA Cloning" cited above. Thus, preferably the cell is supplied with nutrient and cultured at a temperature below 45° C.

The protein product is recovered by conventional methods according to the host cell. Thus, where the host cell is bacterial such as $E.$ $coli$ and the protein is expressed intracellularly, it may be lysed physically, chemically or enzymatically and the protein product isolated from the resulting lysate. Where the host cell is eukaryotic, the product is usually isolated from the nutrient medium.

Where the host cell is bacterial, such as $E.$ $coli$, the product obtained from the culture may require folding for optimum functional activity. This is most likely if the protein is expressed as inclusion bodies. There are a number of aspects of the isolation and folding process that are regarded as important. In particular, the polypeptide is preferably partially purified before folding, in order to minimise formation of aggregates with contaminating proteins and minimise misfolding of the polypeptide. Thus, the removal of contaminating $E.$ $coli$ proteins by specifically isolating the inclusion bodies and the subsequent additional purification prior to folding are important aspects of the procedure.

The folding process is carried out in such a way as to minimise aggregation of intermediate-folded states of the polypeptide. Thus, careful consideration needs to be given to, among others, the salt type and concentration, temperature, protein concentration, redox buffer concentrations and duration of folding. The exact condition for any given polypeptide generally cannot be predicted and must be determined by experiment.

There are numerous methods available for the folding of proteins from inclusion bodies and these are known to the skilled worker in this field. The methods generally involve breaking all the disulphide bonds in the inclusion body, for example with 50 mM 2-mercaptoethanol, in the presence of a high concentration of denaturant such as 8M urea or 6M guanidine hydrochloride. The next step is to remove these agents to allow folding of the proteins to occur. Formation of the disulphide bridges requires an oxidising environment and this may be provided in a number of ways, for example by air, or by incorporating a suitable redox system, for example a mixture of reduced and oxidised glutathione.

Preferably, the inclusion body is solubilised using 8M urea, in the presence of mercaptoethanol, and protein is folded, after initial removal of contaminating proteins, by addition of cold buffer. A preferred buffer is 60 mM ethanolamine containing 1 mM reduced glutathione and 0.5 mM oxidised glutathione. Ideally, the nature of the buffer is determined experimentally in order to obtain a protein product that is functionally active. The folding is preferably carried out at a temperature in the range 1 to 5° C. over a period of 1 to 4 days.

An alternative to the addition of cold buffer is to buffer-exchange the fully reduced protein at room temperature using Sephadex G25 Medium into, for example, 0.3M ethanolamine/1 mM EDTA/1 mM cysteine USP/2 mM L-cystine.2HCl (pH adjustment not required). The solution should be clear, or slightly cloudy -dependent on the level of impurities—and is left static approx 2–30° C. for 1 to 4d. As previously, the exact buffer conditions and temperature should be determined experimentally for each individual protein and are not restricted to those described above.

If any precipitation or aggregation is observed, the aggregated protein can be removed in a number of ways, for example by centrifugation or by treatment with precipitants such as ammonium sulphate.

The polypeptide portion of the derivative of the invention may include a C-terminal cysteine to facilitate post-translational modification. Expression in a bacterial system is preferred for some proteins of moderate size (up to ~70 kDa) and with <~8 disulphide bridges. More complex proteins for which a free terminal cysteine could cause refolding or stability problems may require expression in eukaryotic cells.

The use of insect cells infected with recombinant baculovirus encoding the polypeptide portion is a preferred general method for preparing more complex proteins, particularly the C3d oligomers of the invention.

A preferred method of handling proteins derivatised with cysteine is as a mixed disulphide with mercaptoethanol or glutathione or as the 2-nitro, 5-carboxyphenyl thio-derivative as generally described below.

Where the oligomeric polypeptide derivative of the invention includes a single cysteine, chemical ligation to a second polypeptide containing a unique cysteine may be employed.

The bridge is generated by conventional disulphide exchange chemistry, by activating a thiol on one polypeptide and reacting the activated thiol with a free thiol on the other polypeptide. Such activation procedures make use of disulphides which form stable thiolate anions upon cleavage of the S—S linkage and include reagents such as 2,2' dithiopyridine and 5,5'-dithiobis-(2-nitrobenzoic acid) (DTNB) that form intermediate mixed disulphides capable of further reaction with thiols to give stable disulphide linkages. One polypeptide activated in this way is then reacted with the second containing the free thiol. The precise conditions of pH, temperature, buffer and reaction time will depend on the nature of the reagent used and the polypeptide to be modified. The polypeptide linkage reaction is preferably carried out by mixing the modified polypeptides in neutral buffer in an approximately equimolar ratio. The reaction should preferably be carried out under an atmosphere of nitrogen. Preferably, UV-active products are produced (e.g. from the release of pyridine 2-thione from 2-pyridyl dithio derivatives) so that coupling can be monitored.

After the linkage reaction, the polypeptide conjugate can be isolated by a number of chromatographic procedures such as gel filtration, ion-exchange chromatography, affinity chromatography or hydrophobic interaction chromatography. These procedures may be either low pressure or high performance variants.

The conjugate may be characterised by a number of techniques including low pressure or high performance gel filtration, SDS polyacrylamide gel electrophoresis or isoelectric focussing.

In a further aspect, therefore, the invention provides a process for preparing a derivative according to the invention, this process comprises expressing DNA encoding the oligomeric polypeptide portion of said derivative in a recombinant host cell and recovering the product and thereafter post-translationally linking the polypeptide to a derivatised antigen or other polypeptide.

GENERAL METHODS USED IN EXAMPLES (i) DNA Cleavage

Cleavage of DNA by restriction endonucleases was carried out according to the manufacturer's instructions using supplied buffers (New England Biolabs (U.K.) Ltd., Herts. or Promega Ltd., Hants, UK). Double digests were carried out simultaneously if the buffer conditions were suitable for both enzymes. Otherwise double digests were carried out sequentially where the enzyme requiring the lowest salt condition was added first to the digest. Once the digest was complete the salt concentration was altered and the second enzyme added.

(ii) DNA Ligation

Ligations were carried out using T4 DNA ligase purchased from Promega or New England Biolabs as described in Sambrook et al, (1989) Molecular Cloning; A Laboratory Manual 2nd Edition, Cold Spring Harbor Laboratory Press.

(iii) Plasmid Isolation

Plasmids were isolated using Wizard™ Plus Minipreps (Promega) or Qiex mini or midi kits and Qiagen Plasmid Maxi kit (QIAGEN, Surrey) according to the manufacturer's instructions.

Plasmid pSG.C3d., YL encoding C3d monomer and plasmid pSG.(C3d)$_3$. YL encoding C3d trimer were kindly provided by Professor D. T. Fearon, University of Cambridge.

(iv) DNA Fragment Isolation

DNA fragments were excised from agarose gels and DNA extracted using the QIAEX gel extraction kit or Qiaquick (QIAGEN, Surrey, UK), or GeneClean, or GeneClean Spin Kit or MERmaid Kit, or MERmaid Spin Kit (Bio 101 Inc, California USA) gel extraction kits according to the manufacturer's instructions.

(v) Introduction of DNA Into *E. coli*

Plasmids were transformed into competent *E. coli* BL21 (DE3) or XL1-blue strains (Studier and Moffat. (1986), J. Mol. Biol. 189:113). The *E. coli* strains were purchased as a frozen competent cultures from Stratagene (Cambridge, UK).

(vi) DNA Sequencing

The sequences were analysed by a Perkin Elmer ABI Prism 373 DNA Sequencer. This is an electrophoretic technique using 36 cm×0.2 mm 4% acrylamide gels, the fluorescently labeled DNA fragments being detected by a charge coupled device camera according to the manufactures instructions.

(vii) Production of Oligonucleotides

Oligonucleotides were purchased from Cruachem, Glasgow,UK (viii) Generation of Baculovirus Vectors Plasmids described in this invention having the prefix pBP (e.g. pBP68-01 described below) are used to generate baculovirus vectors and express the encoded recombinant polypeptides by the following methods (Sections (viii) to (x)). Purified plasmid DNA was used to generate recombinant baculoviruses using the kit 'The BacPak Baculovirus Expression System' according to the manufacturers protocols (Clontech, Calif., USA). The insect cell line Sf9 (ATCC) was grown in IPL-41 medium (Sigma, Dorset, UK) supplemented according to manufacturers recommendations with yeast extract, lipids and pluronic F68 (all from Sigma) and 1% (v/v) foetal calf serum (Gibco, Paisley, UK)—this is termed growth medium. Cells were transfected with the linearised baculovirus DNA (supplied in the kit) and the purified plasmid. Plaque assays (see method below) were carried out on culture supernatants and a series of ten-fold dilutions thereof to allow isolation of single plaques.

Plaques were picked using glass Pasteur pipettes and transferred into 0.5 ml aliquots of growth medium. This is the primary seed stock.

(ix) Plaque Assay of Baculoviruses $1 \times 10^6$ Sf9 cells were seeded as monolayer cultures in 30 mm plates and left to attach for at least 30 minutes. Them medium was poured off and virus inoculum in 100 µl growth medium was dripped onto the surface of the monolayer. The plates were incubated for 30 minutes at room temperature, occasionally tilting the plates to prevent the monolayer from drying out. The monolayer was overlaid with a mixture of 1 ml growth medium and 3% (w/v) "Seaplaque" agarose (FMC, ME) warmed to 37° C. and gently swirled to mix in the inoculum. Once set a liquid overlay of 1 ml growth medium was applied. The plates were incubated in a humid environment for 3–5 days.

Visualisation of plaques was achieved by addition to the liquid overlay 1 ml phosphate buffered saline (PBS) containing neutral red solution at 0.1% (w/v) from a stock solution of 1% (w/v) (Sigma, Dorset, UK). Plaques were visible as circular regions devoid of stain up to 3 mm in diameter.

(x) Scale-up of Baculovirus Vectors and Protein Expression

200 µl of the primary seed stock was used to infect $1 \times 10^6$ Sf9 monolayer cell cultures in 30 mm plates. The seed stock was dripped onto the monolayer and incubated for 20 minutes at room temperature, and then overlaid with 1 ml growth medium. The plates were incubated at 27° C. in a humid environment for 3–5 days. The supernatant from these cultures is Passage 1 virus stock. The virus titre was determined by plaque assay and further scale up was achieved by infection of monolayer cultures or suspension cultures at a multiplicity of infection (moi) of 0.1. Virus stocks were passaged a maximum of six times to minimise the emergence of defective virus.

Expression of recombinant proteins was achieved by infection of monolayer or suspension cultures in growth medium with or without foetal calf serum (FCS). Where FCS was omitted cells conditioned to growth in the absence of FCS were used. Virus stocks between passage 1 and 6 were used to infect cultures at a moi of >5 per cell. Typically, infected cultures were harvested 72 hours post infection and recombinant proteins isolated either from the supernatants or the cells.

(xi) Selection of Stable Variants of (C3d)3 Expressed in Insect Cell Using Baculovirus Vectors Baculovirus transfer vector plasmids encoding uncharacterised C3d concatamers containing one or more fuzzy C3d domains are transformed into competent E.coli XL1-blue strain according to Method (v). The resulting colonies each contain a single isolate which may be comprised of one or more fuzzy C3d domains and may also contain one copy of C3d with the original DNA sequence derived from pSG.C3d. YL. Individual colonies are scaled up and DNA extracted according to Method (iii) (miniprep method). Aliquots of DNA are cotransfected into insect cells with BacPak6 linear DNA using a modification of the manufacturers protocol; $2\times10^5$ Sf9 cells are seeded into flat-bottomed microtitre plates and allowed to attach for 30 minutes in serum free medium. If cells are grown in medium containing serum the monolayer is washed three times in serum free medium. The volume of medium in each well is adjusted to a standard volume (typically 50–150 $\mu$l).

Each plasmid isolate 0.5 $\mu$l of miniprep plasmid DNA was taken (at concentrations ranging from 0.5 to 5 $\mu$g/ul) is mixed with 0.1 $\mu$l to 2 $\mu$l of BacPak6 DNA (Clontech) (at concentration supplied) and 5–25 $\mu$l 50 $\mu$g/ml of Lipofectin reagent (Life Technologies Inc.) and incubated at room temperature for 15 minutes to allow lipofectin/DNA complexes to form. The mixture is dripped onto the surface of the medium in a single microtitre well and swirled gently with the pipette tip. A single microtitre dish may contain transfections of up to 96 plasmid isolates, one well per isolate. The transfections are incubated in a humid environment at 27° C. for five hours.

The medium containing the Lipofectin/DNA is then removed from the monolayer and replaced with 100 $\mu$l medium which may contain 1% FCS unless this is considered likely to interfere with subsequent assays. The plate is incubated in a humid environment at 27° C. for three to five days. After three days the plate is visibly inspected for evidence of baculovirus infection. When a significant number of wells show signs of infection (retarded cell growth and enlarged or dumbell-shaped cells) aliquots of culture supernatant art harvested from each well stored under sterile conditions for subsequent expansion. Further aliquots of culture supernatant or cells are subjected to biochemical or biological assay to determine the presence or absence of C3d monomers and oligomers. For example, 20 $\mu$l aliquots of supernatant may be subjected to SDS-PAGE and/or Western blotting (see Methods Section (xii) and (xiv)).

Selected clones showing significant yields of (C3d)3 are scaled up from stored supernatants according to Method (x). Plasmids corresponding to the selected clones are also scaled up for large-scale plasmid DNA extraction according to Method (iii) and sequenced according to Method (vi).

(xii) pBROC413

The plasmid pT7-7 [Tabor, S (1990), Current Protocols in Molecular Biology, F. A. Ausubel, Brent, R. E. Kingston, D. D. Moore, J. G. Seidman, J. A. Smith, and K. Struhl, (eds), pp. 16.2.1–16.2.11, Greene Publishing and Wiley-Interscience, New York.] contains DNA corresponding to nucleotides 2065–4362 of pBR322 and like pBR322 can be mobilised by a conjugative plasmid in the presence of a third plasmid ColK. A mobility protein encoded by ColK acts on the nic site at nucleotide 2254 of pBR322 initiating mobilization from this point. pT7-7 was digested with LspI and BglII and the protruding 5' ends filled in with the Klenow fragment of DNA Polymerase I. The plasmid DNA fragment was purified by agarose gel electrophoresis, the blunt ends ligated together and transformed into *E. coli* DHI by electroporation using a Bio-Rad Gene Pulser and following the manufacturers recommended conditions. The resultant plasmid pBROC413 was identified by restriction enzyme analysis of plasmid DNA.

The deletion in pBROC413 from the LspI site immediately upstream of the f10 promoter to the BglII site at nucleotide 434 of pT7-7 deletes the DNA corresponding to nucleotides 2065–2297 of pBR322. The nic site and adjacent sequences are therefore deleted making pBROC413 non mobilizable.

(xiii) pDB1013

The construction of this plasmid, a derivative of pBROC413, is fully described in Dodd et al (1995) Protein Expression and Purification 6: 727-736.

(xiv) Protein Purification

A number of standard chromatographic techniques can be used to isolate the C3d-containing proteins, e.g. such methods as ion-exchange and hydrophobic interaction matrixes chromatography utilising the appropriate buffer systems and gradient to purify the target proteins. The properties of the C3d containing fusion polypeptides will vary depending on the nature of the fusion protein.

The C3d molecules constructed to contain the C-terminal affinity tag Glu-Glu-Phe can be purified by affinity chromatography using the YL1/2 antibody coupled to Sepharose 4B as described by Dempsey et al (WO 0617625; PCT/GB95/02851).

(xv) Sodium Dodecyl Sulphate Polyacrylamide Gel Electrophoresis (SDS-PAGE)

SDS-PAGE was carried out generally using the Novex system (Novex GmbH, Heidleburg) according to the manufacturer's instructions. Pre-packed gels (4–20% acrylamide gradient, containing a Tris/glycine buffer) were usually used. Samples for electrophoresis, including protein molecular weight standards (for example LMW Kit, Pharmacia, Sweden or Novex Mark 12, Novex, Germany) were usually diluted in 1% (w/v) SDS—containing buffer (with or without 5% (v/v) 2-mercaptoethanol), and left at room temperature for 5 to 30 min before application to the gel.

(xvi) Immunoblotting (a) Dot blot

Immobilon membranes (Millipore, Middlesex, UK) were activated by immersion in methanol for 20 seconds and then washed in PBS for five minutes. The membrane was placed into a vacuum manifold Dot Blotter (Bio-Rad Laboratories, Watford, UK). Crude extracts from cells or culture supernatants were transferred onto the membrane by applying a vacuum and washed through with PBS. Without allowing the membrane to dry out, the Dot Blotter was dismantled and the membrane removed.

(b) Western Blotting

Samples of cell extracts and purified proteins were separated on SDS-PAGE as described in Section (xv). The Immobilon membrane was prepared for use as in (a) above. The gel and the membrane were assembled in the Semi-Dry Transfer Cell (Trans-Blot SD, Bio-Rad Laboratories) with the Immobilon membrane towards the anode and the SDS-PAGE gel on the cathode side. Between the cathode and the gel were placed 3 sheets of Whatman 3M filter paper cut to the size of the gel pre-soaked in a solution of 192 mM 6-amino-n-caproic acid, 25 mM Tris pH 9.4 containing 10% (v/v) methanol. Between the anode and the membrane were placed two sheets of Whatman 3M filter paper cut to the size of the gel and soaked in 0.3M Tris pH 10.4 containing 10% (v/v) methanol next to the anode and on this was laid a further sheet of Whatman 3M filter paper pre-soaked in 25 mM Tris pH 10.4 containing 10% (v/v) methanol.

The whole-assembled gel assembly was constructed to ensure the exclusion of air pockets. The proteins were tranferred from the SDS-PAGE to the Immobilon membrane by passing 200 mA current through the assembly for 30 minutes.

(c) Immunoprobing of Dot Blot and Western Membranes

The membranes were blocked by incubating the membrane for 1 h at room temperature in 50 ml of 10 mM phosphate buffer pH 7.4 cotaining 150 mM NaCl, 0.02% (w/v) Ficoll 400, 0.02% (w/v) polyvinylpyrolidine and 0.1% (w/v) bovine serum albumin (BSA). The appropriate primary antibody was diluted to its working concentration in antibody diluent, 20 mM sodium phosphate buffer pH 7.4 containing 0.3M NaCl, 0.5% (v/v) Tween-80 and 1.0% (w/v) BSA. The membrane was incubated for 2 h at room temperature in 50 ml of this solution and subsequently washed three times for 2 minutes in washing buffer, 20 mM sodium phosphate pH 7.4 containing 0.3M NaCl and 0.5% (v/v) Tween-80. The membrane was then transferred to 50 ml of antibody diluent buffer containing a suitable dilution of the species specific antibody labelled with the appropriate label, e.g. biotin, horse radish peroxidase (HRP), for the development process chosen and incubated for 2 h at room temperature. The membrane was then washed in washing buffer as described above. Finally, the blot was developed according to the manufacturer's instructions.

The appropriate dilution of antibody for both the primary and secondary antibodies refers to the dilution that minimises unwanted background noise without affecting detection of the chosen antigen using the development system chosen. This dilution is determined empirically for each antibody.

(xvii) Measurement of Biological Activity

The biological function of C3d monomer produced in baculovirus can he tested for its ability to hind to its receptor, complement receptor-2 (CR2). As C3d is a product of the process of complement activation and subsequent degradation of C3b by the serum protease Factor I, it was also of interest to test C3d for its possible effect on complement activation using a classical pathway haemolytic assay.

(a) Competitive Binding Assay of C3d to Raji Cells

In this assay the ability of a new construct expressing at least one unit of C3d to compete with a control $^{125}$I-HEL-C3d for CR2 binding sites on the surface of Raji cells, a B-lymphoblastoid cell line, is assessed. Raji cells, $5\times10^7$ to $7\times10^7$ cells/ml are incubated for 1 h at 4° C. with 1 nM $^{125}$I-HEL-C3d and incremental concentrations of C3d containing molecule of interest. The cells are then centrifuged through a dibutyl-diiso-octyl-phthalate cushion, and the amount of radioactivity associated with the pellet determined. From this data the amount of the C3d-containing protein under test necessary to produce a 50% reduction in 1 mM $^{125}$I-HEL-C3d can be determined.

(b) Competitive ELISA demonstrating C3d Binding to CR2

C3d is used to coat 96-well microtitre plates at 5 µg/ml in O. 1M NaHCO$_3$ by incubating overnight at 4° C. The plates are then blocked in 1% BSA 0.1% Tween-20 in PBS for 1 h at room temperature subsequently they are incubated with either 25 µl/well of C3d or from the C3d containing molecule under test in a dose response manner. To the wells is added 25 µl/well of a sub-saturating concentration of co-ligated CR2. IgGl at 125 pM and incubated for 1 h at room temperature. The plates are then washed three times with PBS containing 0.1% (v/v) Tween-20. The amount of CR2 bound to the immobilised C3d is detected using a 1:3000 dilution of HRP-labeled goat anti-mouse-IgGl-antibody in PBS containing 0.1% (v/v)Tween-20 and incubated for 1 h at room temperature the wells were then washed as described above. The presence of HRP-antibody is detected using the TMB Peroxidase EIA Substrate Kit according to the manufacturer's instructions (Bio-Rad, UK).

(c) Anti-complement Activity Measured by the Haemolysis of Sheep Erythrocytes

Measuring the inhibition of complement-mediated lysis of sheep erythrocytes sensitised with rabbit antibodies (Diamedix Corporation, Florida, USA) assesses functional activity of complement inhibitors. Human serum diluted 1:125 or 1:100 in 0.1M Hepes/0.15 M NaCl/0.1% gelatin pH 7.4 was used as a source of complement. The serum was pooled from volunteer blood donations essentially as described in J. V. Dacie & S. M. Lewis. *Practical Haematology*. Churchill Livingstone, Edinburgh. 1975. Briefly, blood (10–20 ml) was warmed to 37° C. for 5 minutes, the clot removed and the remaining serum clarified by centrifugation. The serum fraction was split into small aliquots and stored at −196° C. Aliquots were thawed as required and diluted in the Hepes buffer immediately before use.

Inhibition of complement-mediated lysis of sensitised sheep erythrocytes is measured using a standard haemolytic assay using a v-bottom microtitre plate format as follows:

50 μl of a range of concentrations of inhibitor (typically in the region of 0.1–100 nM) diluted in Hepes buffer are mixed with 50 μl of the diluted serum and 100 μl of sensitised sheep erythrocytes and then incubated for 1 hour at 37° C. Samples are spun at 1600 rpm at ambient temperature for 3 minutes before transferring 150 μl of supernatant to flat bottom microtitre plates and determining the absorption at 410 nm. Maximum lysis (Amax) is determined by incubating serum with erythrocytes in the absence of any inhibitor. Background lysis (Ao) is determined by incubating erythrocytes in the absence of any serum or inhibitor to check whether the inhibitor itself had any effect on lysis, erythrocytes were incubated with inhibitor alone; none of the compounds bad any direct effect on lysis of the erythrocytes. Inhibition is expressed as a fraction of the total cell lysis such that IH50 represents the concentration of inhibitor required to give 50% inhibition of lysis.

$$IH = \frac{A - Ao}{Amax \cdot Ao}$$

where 0 is equivalent to complete inhibition and 1 equals no inhibition.

(xviii) Reduction of Disulphides and Modification of Thiols in Proteins

There are a number of methods used for achieving the title goals. The reasons it may be necessary to carry out selective reduction of disulphides is that during the isolation and purification of multi-thiol proteins, in particular during refolding of fully denatured multi-thiol proteins, inappropriate disulphide pairing can occur. In addition even if correct disulphide paring does occur, it is possible that a free cysteine in the protein may become blocked, for example with glutathione. These derivatives are generally quite stable. In order to make them more reactive, for example for subsequent conjugation to another functional group, they need to be selectively reduced, with for example dithiothreitol (DTT) or with Tris (2carboxyethyl) phosphine.HCl (TCEP) then optionally modified with a function which is moderately unstable. An example of the latter is Ellman's reagent (DTNB) which gives a mixed disulphide. In the case where treatment with DTNB is omitted, careful attention to experimental design is necessary to ensure that dimerisation of the free thiol-containing protein is minimised. Reference to the term 'selectively reduced' above means that reaction conditions e.g. duration, temperature, molar ratios of reactants have to be carefully controlled so that disulphide bridges within the natural architecture of the protein are not reduced. All the reagents are commercially available e.g. from Sigma (Poole, Dorset) or Pierce & Warriner (Chester, Cheshire).

The following general examples illustrate the type of conditions that may be used and that are useful for the generation of free thiols and their optional modification. The specific reaction conditions to achieve optimal thiol reduction and/or modification are ideally determined for each protein batch.

TCEP may be prepared as a 20 mM solution in 50 mM HEPES (approx. pH 4.5) and may be stored at −40° C. DTT may be prepared at 10 mM in sodium phosphate pH 7.0 and may be stored at −40° C. DTNB may be prepared at 10 mM in sodium phosphate pH 7.0 and may be stored at −40° C. All of the above reagents are typically used at molar equivalence or molar excess, The precise concentrations ideally identified experimentally. The duration and the temperature of the reaction are similarly determined experimentally. Generally the duration would be in the range 1 to 24 hours and the temperature would be in the range 2 to 30° C. Excess reagent may be conveniently removed by buffer exchange, for example using Sephadex G25. A suitable buffer is 0.1M sodium phosphate pH 7.0

EXAMPLES

Example 1

Expression and Isolation of Monomeric Murine C3d [(C3d)1] (SEQ ID No. 26) and Trimerie C3d [(C3d)3] (SEQ ID No. 27) in *Escherichia coli*— Evidence for Instability of the Trimeric Construct in a Bacterial Host (a) Construction of Plasmid pDB1033 Encoding (C3d)1 pDB1013 was digested with SpeI/NdeI and the vector fragment was isolated from a 1.1% (w/v) agarose gel and purified using a Qiagen gel extraction kid.

The vector termed pSG.C3d$_1$.YL described in patent WO 96/17625 encodes one copy of the C3d coding sequence preceded by a signal peptide derived from dog pre-proinsulin and is C-terminally tagged by the tripeptide epitope (Glu-Glu-Phe) recognised by the commercially available YL1/2 antibody (Serotec, Oxon). The vector, was cut with BglII and XbaI; the digest was run on a 1.1% (w/v) agarose gel and the 1000 base pairs BglII/XbaI fragment isolated.

These two fragments were ligated wilt the BglII/NdeI linkers (SEQ ID Nos 28 and 29) and transformed into competent *E. coli* JM109 cells under standard conditions and clones isolated.

(b) Expression of (C3d)1 from pDB1033 pDB1033 was transformed into calcium chloride competent *E. coli* BL21(DE3) and resultant colonies were isolated and checked for plasmid content. To express protein from pDB1033 in *E. coli* BL21(DE3), a single colony was inoculated into 10 ml LB media (20 g/l tryptone, 15 g/l yeast extract, 0.8 g/l NaCl. 0.2 g/l Na$_2$HPO$_4$, 0.1 g/l KH$_2$PO$_4$ containing 50 μg/ml ampicillin (Sigma). The culture was grown for 6 hours at 37° C. 260 rpm before being used to inoculate 100 ml of the same media containing 50 μg/ml ampicillin. Growth was under the same conditions overnight. 25 ml of each culture was then used to inoculate 3×500 ml of the same media with 50 μg/ml ampicillin in 31 Erienmeyer flasks. Cells were grown to an OD of about 1.2 at $A_{600}$ nm. IPTG (isopropyl β-D galactopyranoside) was added to a final concentration of 1 mM and cells incubated for a further about 3.5 hours before harvesting by centrifugation at 8000 g/10 minutes. Cell pellet from 1.51 of culture was processed immediately.

(e) Isolation of (C3d)1

The methods described are essentially those detailed for the isolation of SCR1–3 of Complement Receptor 1 in Dodd. et al (1995) Protein Expression and Purification 6: 727-736, with some modifications.

(i) Isolation of Solubilised Inclusion Bodies

The cell pellet of *E. coli* BL21(DE3)(pDB1033) was resuspended in 50 mM Tris/50 mM NaCl/1 mM EDTA pH 8.0 (approximately 150 ml). The suspension was transferred to a glass beaker surrounded by ice and sonicated (Heat systems—Ultrasonics W380; 50×50% pulse, pulse time=5 seconds.) for 3 minutes and then spun at 15000 g for 10 minutes. The supernatant was decanted and discarded. The inclusion body pellet was stored at −40° C. for 7 days. It was then resuspended in 20 mM Tris/8M urea/1 mM EDTA/50 mM 2-mercaptoethanol pH 8.5 (120 ml) at room temperature by vigorous swirling, then left for 2 hours at room temperature with occasional swirling.

(ii) Initial Purification Using Macroprep High Q

To the viscous solution was added Macroprep High Q (Bio-Rad; 24 g wet weight) that had been water washed and suction-dried. The mixture was swirled vigorously and left static for 1–2 h at room temperature. The supernatant was decanted, sampled and discarded. The remaining slurry was resuspended to a uniform suspension and poured into a glass jacket and allowed to settle into a packed bed. The column was equilibrated with 0.02M. Tris/8M urea/0.05M 2-mercaptoethanol/0.001M EDTA pH 8.5 at room temperature. When the $A_{280}$ of the eluate had stabilised at baseline, the buffer was changed to equilibration buffer additionally containing 1M NaCl. A single $A_{280}$ peak was eluted by the 1M NaCl-containing buffer, the volume was approximately 80 ml. SDS-PAGE under reducing conditions showed the product contained one major species, weight a molecular weight around 35000. The solution was stored at −40° C.

(d) Construction of Plasmid pDB1032 Encoding (C3d)3 pDB 1013 was digested with SpeI/NdeI and the vector fragment isolated from a 1.1% (v/w) agarose gel and purified using a Qiagen gel extraction kit.

The vector termed pSG.(C3d)3 YL described in patent WO 96/17625 encodes three identical copies of the C3d coding sequence preceded by a signal peptide derived from dog pre-pro-insulin. The C3d domains are separated by a linker $(Gly_4\text{-}Ser)_2$, and there is tripeptide epitope (Glu-Glu-Phe) at the C-terminal of the final C3d domain that is recognised by the commercially available YL1/2 antibody (Serotec, Oxon.). The vector was cut with BglII And XbaI; the digest was run on a 1.1% (v/w) agarose gel and the 3000 base pairs BglII/XbaI fragment isolated. These two fragments were ligated with the BglII/NdeI linkers (SEQ ID Nos 28 and 29) and transformed into competent *E. coli* JM109 cells under standard conditions and clones containing pDB1032 were isolated. The amino acid sequence encoding C3d3 is described in Sequence ID 27.

(b) Expression of (C3d)3 from pDB1032 pDB1032 was transformed into calcium chloride competent *E. coli* BL21(DE3) and resultant colonies were isolated and checked for plasmid content. To express protein from pDB 1032 in *E. coli* BL21(DE3), a single colony was inoculated into 10 ml LB-phosphate (20 g/l tryptone, 15 g/l yeast extract, 0.8 g/l NaCl. 0.2 g/l $Na_2HPO_4$, 0.1 g/l $KH_2PO_4$) containing 50 µg/ml ampicillin. The culture was grown overnight at 37° C., 230 rpm, before being used to inoculate 50 ml of the same medium containing 50 µg/ml ampicillin. Growth was under the same conditions overnight. 15 ml of each culture was then used to inoculate 3×600 ml of the same medium with 50 µg/ml ampicillin in 3l Erlenmeyer flasks. Cells were grown to an OD of about 1.1 at $A_{600}$ nm. IPTG was added to a final concentration of 1 mM and cells allowed to continue growth for a further about 3.5 hours before harvesting by centrifugation at 8000 g/10 minutes. Pellet from 1.5l of culture was processed immediately.

(c) Isolation of (C3d)3

The methods described are essentially those detailed for the isolation of SCR1-3 of Complement Receptor 1 in Dodd et al (1995) Protein Expression and Purification 6: 727-736, with some modifications.

(i) Isolation of Solubilised Inclusion Bodies

The cell pellet of *E. coli* BL21(DE3)(pDB1032) was resuspended in 50 mM Tris/50 mM NaCl/mM EDTA pH 8.0/0.1 mM PMSF (approx. 100 ml). The suspension was transferred to a glass beaker surrounded by ice and sonicated (Heat systems—Ultrasonics W380; 50×50% pulse, pulse time=5 seconds.) for 3 minutes and then spun at 15000 g for 10 minutes. The supernatant was decanted and discarded. The inclusion body pellet was stored at −40° C. For 3d. It was then resuspended in 20 mM Tris/8M urea/1 mM EDTA/ 50 mM 2-mercaptoethanol pH 8.5 (120 ml) at room temperature by vigorous swirling, then left for 2 h at room temperature with occasional swirling.

(ii) Initial Purification Using Macroprep High Q

To the viscous solution was added Macroprep High Q (Bio-Rad; 24 g wet weight) that had been water washed and suction-dried. The mixture was swirled vigorously and left static for 1–2 h at room temperature. The supernatant was decanted, sampled and discarded. The remaining slurry was resuspended to a uniform suspension and poured into a glass jacket and allowed to settle into a packed bed. The column was equilibrated with 0.02M Tris/8M urea/0.05M 2-mercaptoethanol/0.001M EDTA pH 8.5 at room temperature. When the $A_{280}$ of the eluate had stabilised at baseline, the buffer was changed to equilibration buffer additionally containing 1M NaCl. A single $A_{280}$ peak was eluted by the 1M NaCl-containing buffer; the volume was approximately 80 ml. SDS PAGE under reducing conditions showed that the product contained one major species, with a molecular weight around 35000, and additional species with molecular weights close to the target molecular weight of around 105000 and believed to be the target species. The solution was stored at −40° C.

These results show that expression in a bacterial host of either monomeric or trimeric C3d genes gives rise to substantially the same product—the monomeric protein. The origins of this instability were not determined in this experiment.

Example 2

Expression and Isolation of C3d Oligomers Expressed in Insect Cells Using Baculovirus Vectors Evidence for Homologous Recombination as the Origin of the Low Yield of Trimer and the High Yield of a Monomeric C3d Form (a) Construction of Plasmid pBP68-01 Encoding (C3d) 3EEF The vector termed $pSG.(C3d)_3$. YL described in patent WO 96/17625 encodes three identical copies of the C3d coding sequence preceded by a signal peptide derived from dog pre-pro-insulin. The C3d domains are separated by a linker $(Gly_4\text{-}Ser)_2$, and there is tripeptide epitope (Glu-Glu-Phe) at the C-terminal of the final C3d domain that is recognised by the commercially available YL1/2 antibody (Serotec, Oxon.)

$PSG.(C3d)_3$. YL was digested with restriction endonucleases EcoRI ad XbaI and the 3075 base pairs band was isolated from an 1% (w/v) agarose gel using GeneClean extraction kit according to the manufacturer's instructions. The baculovirus expression vector pBacPak8 (Clontech) was digested with restriction endonucleases EcoRI and XbaI and the 5.6 k base pairs band was isolated from a 0.7 (w/v) agarose gel.

The two fragments were ligated with T4 DNA ligase to give pBP68-01. The ligated plasmid was transformed into competent *E. coli* XL1-blue purchased from Stratagene. Ampicillin resistant transformants were selected on LB-agar plates containing 50 µg/ml ampicillin. Resulting colonies were analysed by restriction endonuclease digestion Plasmid DNA was extracted from *E. coli* containing pBP68-01 using Qiaex mini or midi prep kits according to manufacturer's protocols.

b) Generation of Baculovirus pBP68-01 for Expression of C3d Oligomers

Purified pBP68-01 plasmid DNA was used to generate a recombinant baculovirus expression vector for (C3d)3-YL as described in General Methodology Section (viii). Resulting plaques were picked and used to generate primary seed stocks. Recombinant baculoviruses expressing C3d oligomers were identified by immuno-dot blot of culture supernatants of Passage 1 virus stocks, probing with an antibody to human C3d obtained from Dako (Ely, Cambs) at a dilution of 1 in 2000 the blot was developed using the ECL kit (Amersham, Middlesex). Those showing a positive signal on the dot blot were further scaled up and used to generate Passage 3 or 4 working stocks with virus titres between $10^7$ and $10^9$ plaque forming units (pfu) per ml.

c) Expression of C3d Oligomers in Insect Cells

Sf9 cells adapted for growth in the absence of serum were grown in suspension culture to a cell density of $1.5 \times 10^6$ cells/ml in 4×50 ml of media in 200 ml Erlenmeyer flasks shaken at 20 rpm. These cells were then infected by addition of $1 \times 10^9$ pfu/ml Passage 3 working stocks to give a final concentration of 5 pfu/cell. The supernatant 72 hours post infection was found to contain three species of C3d oligomer. (C3d)3, as encoded in the original vector, in trace amounts, (C3d)2, also in trace amounts and C3d monomer relatively large amounts (5–10 mg/l). The harvest medium 210 ml, was stored at −40° C. until further processed.

d) Purification of C3d from S19 Baculovirus Harvest Media

Approximately half the harvest supernatant, 113 ml, was adjusted to pH 7.4 with 10M NaOH and the conductivity of the solution measured usually the salt concentration was below 0.1M if it was above this concentration the solution was diluted with the appropriate amount of 50 mM Hepes pH 7.4 to bring the salt concentration to 80 mM.

The harvest supernatant was loaded onto a Macroprep-high-Q column, bed volume; 25 ml pre equilibrated in 50 mM Hepes pH 7.4 and then washed with 50 mM Hepes pH 7.4 until the baseline stabilised. The linear flow rate for loading and washing the column was 89 cm/h and was decreased to 60 cm/h during elution. The bound proteins were eluted with a linear 0–1M NaCl over 10 column volumes and 5 ml fractions collected. The column material was heavily contaminated with medium components and was discarded after a single use.

The C3d eluted between 0.15M and 0.3M NaCl as revealed by reducing SDS-PAGE. The fractions eluting between 0.15M NaCl and 0.2M NaCl were 50% pure, (C3d)2 and (C3d)3 eluted after the C3d1. The C3d1 pooled fractions, 40 ml, were concentrated to 2 ml by using 40 ml ultrafiltration stirred cell containing a YM10 membrane (Amicon, Glos.). No further purification was performed prior to characterisation of the product, Sections (d) and (e) below.

e) Physiochemical Characterisation of the Monomeric Species (i) N-Terminal Sequence A sample containing the monomeric C3d was separated on a reducing SDS-PAGE. The proteins were electrotransferred to a Problott (Applied Biosystems) as described in General Methods (Section (xvi) (b)). Post electrotransfer the membrane was rinsed in 100% methanol for 10 s and then stained with a solution containing 0.1% (w/v) amido black (Sigma), 40% methanol, 1% acetic acid for 30 s and subsequently destained by a 50% methanol solution. The band corresponding to the C3d monomer was excised. The N-terminal sequence of the protein was analysed by Edman Degradation using a Beckman Automatic Amino Acid Analyser (Beckman). A single N2-terminal sequence was obtained, this sequence corresponded to 25 to 44 of the C3d1 sequence expressed in Baculovirus/Sf9 cells (SEQ ID. No.37) and indicated as expected the secreted monomer had its signal sequence removed.

(ii) Mass Spectrometry

The mass of the C3d was determined by electrospray mass spectrometry on a solution containing the purified C3d. A single pack was found with a mass of 34279 Da. This corresponds to a sequence starting at the N-terminal sequence as described in Section (d) (i) above but containing the C-terminal antibody affinity tag (Glu-Glu-Phe). This sequence shown below (SEQ ID no.37).

(iii) Western Blotting

The purified C3d was western blotted according to the methods described in Section (xvi) (b) following separation on a reducing SDS-PAGE. The blot was probed with primary antibodies to C3d and the affinity tag Glu-Glu-Phe.

(1) C3d Antibody Primary rabbit polyclonal antibody to human C3d (Dako, Cambs. UK) and the secondary antibody a biotin-labelled polyclonal goat anti-rabbit IgG antibody (Amersham Bucks.) were used at 1:500 dilution of the stock. The blot was developed using the Immunogold Silver Staining Kit (Amersham) according to the manufacturer's instructions. The developed blot showed a single immunoreactive band corresponding to the correct position of the C3d nonomer on the SDS-PAGE.

(2) Antibody to Affinity Tag. Monoclonal rat antibody from clone YL1/2 (Serotec) recognising the C-terminal tag Glu-Glu-Phe was used a 1:500 dilution to probe the immunoblot. The secondary antibody biotin-labelled polyclonal goat anti-rat antibody was used at a dilution of 1:1000. The blot was developed using the Immunogold Silver Staining Kit (Amersham) according to the manufacturer's instructions. The developed blot showed a single immunoreactive band corresponding to the correct position of the C3d monomer on the SDS-PAGE. This result indicated the presence of the epitope tag in a major proportion of the C3d monomers.

These Sections (i to iii) suggest the C3d expressed in harvest supernatant contains the N-terminal of the first C3d unit containing the signal sequence encoded in the plasmid pBP68-01 and the C-terminal of the molecule the information encoded by the third unit of C3d containing the affinity tag in the plasmid. The amino acid sequence of this combination is described in SEQ ID no. 37.

(f) Biological Assay of the C3d Monomer)

The biological function of C3d monomer produced in baculovirus was tested by its ability to bind to its receptor, complement receptor-2(CR2).

(i) Competitive Binding Assay of C3d to Raji Cells

The binding was performed as described in General Methods Section (xvii) (a). The amount of radioactivity associated with the cell pellet was used to construct a binding curve of $^{125}$I-HEL-C3d bound to the Raji cells, this showed a 50% reduction in binding of the label was achieved using of binding concentration of 2.5 $\mu$M of either the baculovirus/Sf9 C3d or C3d expressed in COS cells.

(ii) ELISA demonstrating C3d Binding to CR2

The ELISA was performed as described in General Methods Section (xvii) (b). The monomer gave a $I_{50}$ of 2 $\mu$M for the baculovirus/Sf9 material. A similar figure was obtained for the COS cell produced C3d.

(iii) Anti Haemolytic Activity of C3d

The anti-haemolytic assay was performed as described in the General Methods Section (xvii) (c) on a purified sample of C3d1. The C3d1 protein product inhibited complement-mediated lysis of sensitised sheep red blood cells with an IH50 of approximately 700 nM. The C3d activity in this assay is probably as a competitive inhibitor of C3 the complement pathway.

The data described in this Section provides evidence that C3d produced in the baculovirus/Sf9 expression system is equivalent in activity to that produced in COS cells. However this system produces at least 50-fold more C3d per litre than the COS system offering significant fermentation savings.

(g) Characterisation of Baculovirus Vector Produced from pBP68-01

Characterisation of the monomeric protein led to the hypothesis that homologous recombination had occurred within the repeated C3d coding sequence in the baculovirus vector leading to deletion of two copies of C3d. PCR analysis was used to characterise the viruses present in the cultures, which produced the monomeric species.

DNA was extracted from the cell pellets from 50 ml samples from two independent production runs. The cells were suspended in 5 ml of a solution containing 10 mM Tris, 10 mM EDTA, 100 μg/ml proteinase K pH 7.6. After re-suspension SDS was added to 0.5% (w/v), mixed gently to avoid shearing the DNA and incubated for 60 minute at 37° C. An equal volume of phenol: chloroform: isoamyl alcohol 1:24:1, (Sigma) was added and mixed by inversion for 5 minutes then centrifuged at 12000 g for 5 minutes. The upper aqueous layer was transferred to a clean tube and a 0.6 volume of isopropanol was added to precipitate the DNA. A clot of DNA was produced which was transferred into 5 ml 80% (v/v) ethanol for 1 minute. The ethanol was poured off and drained without allowing the pellet DNA clot to dry completely. The DNA clot was dissolved in 1 ml deiomised water containing 50 units of RNase A (Sigma).

A PCR reaction was carried out to determine the length of the DNA encoding C3d. The primers used for the PCR were homologous to sequences flanking the coding region, corresponding to the position of the EcoRI and XbaI restriction sites used in the cloning. The sequence of the forward primer #39171 was GAATTCCTAGCTTGCTTG (SEQ. ID No 30) and the reverse primer #39172 was TCTAGAGTCGACCA-GAC (SEQ. ID No. 31). The PCR conditions were as follows: 1 μl DNA solution (from cell pellets), 1 μl 10 mM dNTPs. 50 pMol each of forward and reverse primers (SEQ. ID no. 30 and 31), 5 μl×10 Taq polymerase buffer (Promega), 3 μl 25 mM MgCl$_2$, deionised water to 49 μl and 1 μl Taq polymerase (5 units) (Promega). PCR was carried out in a thermal cycler with the following cycle: Step 1: 95° C. for 1 minute, Step: 2 95° C. for 30 seconds, Step 3: 55° C. for 30 seconds, Step 4: 72° C. for 1 minute, Step 5: 72° C. for 5 minutes. Steps 2–4 were repeated 30 times prior to step 5. A tenth of the products were run on 1% (w/v) agarose gels. The expected size for (C3d)3 was 3088 base pairs and for C3d monomer was 1217 base pairs. The PCR product of the reactions was clearly a 1217 base pairs band with no evidence of a 3088 base pairs band.

These data, and the protein characterisation data strongly suggest that a homologous recombination event has occurred resulting in the deletion of two of the three C3d genes, leaving the signal peptide and the amino terminal portion of the first domain and the carboxy terminal portion and the Glu-Glu-Phe tag of the third domain. The point of crossover is impossible to determine as the coding sequences in the three copies of C3d are identical.

Subsequent attempts to isolate a stable virus containing three C3d domains by plaque cloning were unsuccessful. All viruses rocovered contained only the single C3d domain determined by PCR analysis as described above.

Example 3

Design and Construction of a Fuzzy Gene Encoding C3d Monomer (a) Synthetic Gene Design Homologous recombination occurs as a result of DNA strand exchange between regions of homology. In the present invention a series of synthetic C3d domains are constructed in such a way to reduce to a minimum to presence of homologous DNA when the sequences are concatenated, without altering the coding sequence of the C3d domain. The basis of the invention is to utilise the third base "wobble" phenomenon to introduce silent changes throughout the domain. The number of possible variants of this is very large, and not cannot be specified individually. Where third base "wobble" is introduced the variations shown in Table 1 are included. Certain third base "wobble" options are specifically avoided where a codon was found to be rare in mammalian, insect or bacterial genomes. Codons with variable third base positions are described hereinafter as "fuzzy" codons.

TABLE 1

| Amino acid | Codon | Rare codons | fuzzy codon | reverse fuzzy codon |
|---|---|---|---|---|
| Ala | GCN | none | GCN | NGC |
| Arg | CGN or AGR | CGG[2,3] CGA[1,2,3] | CGY | RCG |
| Asn | AAY | none | AAY | RTT |
| Asp | GAY | none | GAY | RTC |
| Cys | TGY | none | TGY | RCA |
| Gln | CAR | none | CAR | YTG |
| Glu | GAR | none | GAR | YTC |
| Gly | GGN | none | GGN | NCC |
| His | CAY | CAT[2] | CAC | GTG |
| Ile | ATH | ATA[3] | ATY | RAT |
| Leu | CTN or TTR | CTA[1,2,3] | CTB | VAG |
| Lys | AAR | none | AAR | YTT |
| Phe | TTY | none | TTY | RAA |
| Pro | CCN | CCC[3] CCG[1,] | CCW | SGG |
| Ser | TCN or AGY | TCG[1] | TCH | DGA |
| Thr | ACN | none | ACN | NGT |
| Tyr | TAY | none | TAY | RTA |
| Val | GTN | none | GTN | NAC |

NB: The codons for Met (ATG) and Trp (TGG) are invariant.
Key:
[1]Rare codon in mammalian genome
[2]Rare codon in insect genome
[3]Rare codon in bacterial genome
R  A or G
Y  C or T
S  C or G
W  A or T
H  A or C or T
B  C or G or T
V  A or C or G
D  A or G or T
N  A or C or G or T Twelve oligonucleotides ranging from 76 to 106 bases in length were synthesised encoding the upper or lower strand of the C3d sequence. Oligonucleotide Fuz1 (SEQ. ID No 1) encoded the first 79 bases of the C3d sequence (forward strand) preceded by 21 bases including a BglII site (in frame with the BglII site in pBP68-01) and a NdeI site (in frame with the NdeI site in pDB1032 and pDB1033). Of the 26 C3d amino acids codons present in Fuz1, the first 20 are encoded by fuzzy codons (with the exception of the invariant methionine codon ATG). The carboxy terminal 14 residues of Fuz1 are invariant, with codons selected where possible to be GC rich to enhance annealing of these complementary sequences. This region represents the region of overlap with Fuz2 (Seq. ID No 2). Oligonucleotide Fuz2 encodes amino acids 23 to 54 of C3d (reverse stand) where the reverse codons for amino acids 23–26 at the 3' end are invariant and overlap Fuz1. Amino acids 27 to 49 are encoded by reverse fuzzy codons (with the exception of the invariant tryptophan reverse codon CCA). At the 5' end the terminal 14 residues of Fuz2 are invariant, with reverse codons selected where possible to be GC rich. This region represents the region of overlap with Fuz3.

Fuz3 through to Fuz11 (SEQ. ID No 3 to No 11) were designed along similar lines, with a central region of fuzzy codons and invariant, GC-rich ends overlapping by 13–17 bases with the flanking oligonucleotides.

Fuz12 (SEQ ID NO: 12) overlaps with Fuz11 at the 3' end by 14 bases and has the central region of fuzzy codons encoding C3d, but the 5' end of the oligonucleotide which represents the carboxy terminus of the gene contains a linker region (Gly-Gly-Gly-Gly-Ser (SEQ ID NO: 47) (in fuzzy codons), a BamHI site, a stop codon and an EagI site. The BamHI site allows for subsequent fusion to the amino-terminal BglII site of another C3d domain for concatenation of multiple domain. The stop codon will be retained only in the carboxy-terminal C3d domains, and the EagI site allows for subsequent cloning into the baculovirus vector pBac-Pak8.

(b) Gene Assembly

The fuzzy C3d gene was built in stages involving cycles of annealing and amplification using the polymerase change reaction (PCR) methodology these amplified segments are then ligated together.

In the first stage the fuzzy oligonucleotides were annealed in pairs through their GC-rich invariant overlapping regions in the following combinations; Fuz1+Fuz2, Fuz3+Fuz4, Fuz5+Fuz6, Fuz7+Fuz8, Fuz9+Fuz 10, Fuz 11+Fuz12. To amplify the paired fuzzy oligonucleotides PCR primers were designed each stand at the overlapping invariant GC rich region at the 5' end of the odd numbered oligos and to the 3' end of the even-numbered oligos. These PCR primers incorporated base changes that created novel restriction sites at each end of the overlapping pairs of fuzzy oligonucleotide. This property allowed trimming of the amplified DNA sequences by specific endonucleases to give cohesive ends that anneal the amplified fuzzy oligonucleotides in their correct orientation. An alternative PCR primer to Fuz12 termed Fuz25 (SEQ. ID No.25) was identical to Fuz 12 except at its 5' end an additional codon was added prior to the stop codon to incorporate a C-terminal cysteine residue. This C-terminal cysteine in the expressed protein could be used subsequently to couple antigen to the C3d$_n$ The PCR primers are listed in the Table 2 below showing the fuzzy oligonucleotide pairs they are designed to amplify and their unique restriction site:

TABLE 2

PCR primers designed to amplify fuzzy oligonucleotide overlapping pairs

| Fuzzy oligonucleotide overlapping pairs | PCR primer | Strand | Novel restriction site |
|---|---|---|---|
| Fuz1 + Fuz 2 | Fuz23 (SEQ ID No. 23) | forward | None |
|  | Fuz20 (SEQ ID No. 20) | reverse | PvuII |
| Fuz3 + Fuz4 | Fuz19 (SEQ ID No. 19) | forward | PvuII |
|  | Fuz14 (SEQ ID No. 14) | reverse | XhoI |
| Fuz5 + Fuz6 | Fuz13 (SEQ ID No. 13) | forward | XhoI |
|  | Fuz16 (SEQ ID No. 16) | reverse | XmaI |
| Fuz7 + Fuz8 | Fuz15 (SEQ ID No. 15) | forward | XmaI |
|  | Fuz18 (SEQ ID No. 18) | reverse | XmaI |

TABLE 2-continued

PCR primers designed to amplify fuzzy oligonucleotide overlapping pairs

| Fuzzy oligonucleotide overlapping pairs | PCR primer | Strand | Novel restriction site |
|---|---|---|---|
| Fuz9 + Fuz10 | Fuz17 (SEQ ID No. 17) | forward | BclI |
|  | Fuz22 (SEQ ID No. 22) | reverse | HindIII |
| Fuz11 + Fuz12 | Fuz21 (SEQ ID No. 21) | forward | HindIII |
|  | Fuz24 (SEQ ID No. 24) | reverse | None |
|  | Fuz25 (SEQ ID No. 25) | reverse | None |

The PCR reactions were all carried out under identical conditions for each reaction containing a single pair of overlapping fizzy oligonucleotides. The PCR reaction was carried out in a total reaction volume of 0.6 ml containing fuzzy oligonucleotides at a final concentration of 1 nM and the PCR oligos at 2 μM in the combinations as described in Table 2 above, to this was added 48 μl 2.5 mM dNTPs, 60 μl×10 Taq polymerase buffer (Promega), 48 μl 25 mM MgCl$_2$, deionised water to 49 μl and 6 μl Taq polymerase (30 units) (Promega), sterile deionised water was added to give a final volume of 0.6 ml. The temperature cycling was identical for all reactions: 94° C. for 5 min followed by 35 cycles of 50° C./2 min; 72° C./3 minutes; 94° C./1 minutes; this was followed by an incubation at 72° C. for 7 minutes.

The PCR reaction products were separated on a 1.3% (w/v) agarose gel and the amplified product at the correct size was excised from the gel and purified using either MERmaid Kit or MERmaid Spin Kit into 60 μl of sterile deionised water.

The purified products from the PCR reaction were restriction endonuclease digested with the appropriate enzyme see Table 2 above to provide cohesive ends for ligation. Post restriction enzyme digest the DNA was buffer exchanged into 30 μl sterile deionised water by purifying the DNA from solution using either MERmaid Kit or MERmaid spin Kit.

The PCR products whose restriction sites were compatible with appropriately cut pBluescript II SK+ (Stratagene) were ligated. The ligated DNAs were transformed into competent E. coli XL1-blue purchased from Stratagene. Ampicillin resistant transformants were selected on LB-agar plates containing 50 μg/ml ampicillin. Plasmid DNA extracted from the resulting colonies were identified initially by restriction enzyme digest to confirm insertion of PCR product and then the sequence of the fuzzy variants was determined by DNA sequencing.

Alternatively, the fuzzy C3d fragments were generated using the fuzzy oligonucleotide pairs and PCR primers as described above in a modified reaction using Pfu Turbo polymerase (Stratagene). The PCR reaction was carried out in a total reaction volume of 100 μl containing fuzzy oligonucleotides at a final concentration of 1 nM and the PCR oligos at 2 μM in the combinations as described in Table 2 above, to this was added 4 μl 5 mM dNTPs, 10 μl×10 Pfu polymerase buffer (Stratagene), deionised water to 99 μl and 2 μl Pfu Turbo polymerase (20 units) (Stratagene). The temperature cycling was identical for all reactions: 95° C. for 5 min followed by 30 cycles of 50° C./1 min; 68° C./1 minutes; 95° C./1 minutes; this was followed by an incubation at 68° C. for 7 minutes. The resulting products, typically 180–200 base pairs in length, were purified from 1.5% agarose gels using Gene-Clean Spin columns (Bio101) according to manufacturers instructions.

The purified fragments were used to mutagenise the vector pBP66-01, thereby introducing patches of fuzzy sequence into the wild-type sequence using QuickChange mutagenesis (Stratagene) using a modification of the manufacturer's protocol. A mutagenesis reaction typically contained 0.5 µg fuzzy DNA fragment, 0.5 µg pBP66-01, 2 µl 5 mM dNTP, 5 µl buffer supplied in the kit, deionised water to 49 µl and 1 µl Pfu Turbo polymerase (10 units) (Stratagene). Cycling conditions and subsequent steps were as described in manufacturers protocols for multiple mutations. The reaction was transformed into competent *E. coli* XL1-blue purchased from Stratagene. Ampicillin resistant transformants were selected on LB-agar plates containing 50 µg/ml ampicillin. Plasmid DNA extracted from the resulting colonies is identified initially by restriction enzyme digest and confirmed by DNA sequencing. Repeated rounds of mutagenesis with different fuzzy fragments is carried out, followed by error correction using QuickChange mutagenesis using standard manufacturers protocols. After several rounds of mutagenesis and sequencing a library of complete fuzzy C3d genes is obtained from which are selected those with correct sequence and maximum variation from the wild type C3d sequence.

Example 4

Construction and Expression of Fuzzy Genes Encoding (C3d)3 Using Variants of the C3d Sequence (a) Construction of the pBP68-30 Series: Baculovirus Vectors for (C3d)3 Which are Resistant to Homologous Recombination pBP68-30 through to pBP68-39 contain three different variants of the C3d sequence that have been demonstrated by repeated passage in insect cells to be resistant to homologous recombination, see General Methods Section (ix), by virtue of sequence variation introduced at the third base "wobble" position in the first and second C3d domains. The pBP68-30 series of plamids were constructed in two steps. In the first step, pBP68-01 was digested with the restriction enzyme SacI which cleaves once within each C3d domain. The 6725 base pairs vector fragment was purified and self-ligated to form pBP66-01, pBP66-01 contains a single C3d domain containing a signal peptide at the amino terminus and the Glu-Glu-Phe tag at the carboxy terminus, pBP66-01 was transformed into XL-1blue *E. coli* and DNA extracted from the resulting colonies analysed by restriction digest.

In the second step pBP66-01 is digested with the restriction enzyme BglII. Fuzzy C3d domains or fragments were assembled as described in Example 3(b). PCR fragments or full-length products or plasmid vectors into which such products have been subcloned were digested with BamHI and BglII and DNA fragments of 936 base pairs encoding single fuzzy C3d domains were purified and ligated with this fragment. Smaller fragments of fuzzy C3d may also be generated in Example 3(b) and these are digested with appropriate restriction enzymes to generate compatible cohesive ends to reconstruct a full length fuzzy C3d domaim.

The sequence of individual variants of the fuzzy C3d domains may be determined prior to this ligation following subcloning into a holding vector such as pBC00-02 (see below) or the ligation may be carried out using uncharacterised and potentially heterogeneous mixture of PCR products gene in Example 3 (b).

The resulting plasmids are designated p BC66-10 to 19 where a single fuzzy C3d domain is cloned into pBC00-02, pBP67-20 to pBP67-29 where the vector contains one fuzzy C3d domain and one invariant C3d domain, or pBP68-30 to pBP68-39 where the vector contains two different fuzzy C3d domains and one invariant C3d domain.

As an alternative strategy, the plasmid pBP66-01 is subjected to site directed mutagenesis to introduce unique restriction enzyme sites corresponding to the restriction enzyme sites engineered into the termini of the PCR products representing sub-domains of fuzzy C3d described in Table 2 such that the PCR primer pair Fuz13 and Fuz14 (SEQ ID Nos. 13/14) are used to generate a novel XhoI site at position 1713 in pBC66-01, numbering according to SEQ ID No.32; the PCR primer pair Fuz15/Fuz16 (SEQ ID Nos. 15/16) are used to generate a novel XmaI site at position 1866 in pBC66-01, the PCR primer pair Fuz17/Fuz18 (SEQ ID Nos.17/18) are used to generate a novel BclI site at position 2060 in pBC66-01; the PCR primer pair Fuz21/Fuz22 (SEQ ID Nos.21/22) are used to generate a novel HindIII site at position 2222 in pBC66-01. These restriction sites and a unique PvuII site present in the invariant sequence at position 393 are utilised to excise specific fragments of the invariant C3d sequence. These are replaced with corresponding fuzzy C3d fragments generated in Example 3 (b) having compatible cohesive ends, identical amino acid coding sequence, but fuzzy DNA sequence at the third base "wobble" position as described in Example 3 (a).

The resulting plasmids where the restriction sites are introduced into invariant C3d sequence are designated pBP66-02 (XhoI site) pBP66-03 (XmaI site), pBP66-04 (BclI site), pBP66-05 (HindIII site).

(b) Expression of (C3d)3 Using Fuzzy Gene Variants of the C3d Sequence in Baculovirus/Sf9 System Recombinant baculoviruses are generated from the plasmids constructed as described in Section (a), this example, and used to express the encoded polypeptide according to the methods described in "General Methodology used in examples" Sections (viii) to (x).

(c) Purification and Characterisation of the (C3d)3 Expressed from the Fuzzy Variants The (C3d)3 protein is purified as described in Section (xiv) of General Methods. The purified protein is characterised biologically by the methods described in Section (xvii) and physically characterised as described in Sections (xv) and (xvi) (b–c) and its exact mass determined by mass spectrometry. N-terminal sequence is also determine (d) Construction of the pBC66-10, pBC67-10, pBC68-10: *E.coli* vectors for (C3d)3 which are Resistant to Homologous Recombination pBroc413 is digested with the restriction endonucleases NdeI and PstI and the vector fragment isolated from a 0.9% (w/v) agarose gel. To create a new multi-cloning sites suitable for exchange of C3d variants between the pBakPak8 vector and a bacterial expression vector a new polylinker site described in SEQ ID no. 38 and 39 is ligated into the vector fragment. This new vector is called pBC00-02.

The plasmids designated pBP68-10 to 19 encode one fuzzy C3d domain. The series pBP67-20 to 29 encode one fuzzy C3d variant and the native C3d sequence and pBP68-30 to 39 contain two fuzzy C3d variant and a native the C3d sequence. These plasmids are digested with the restriction endonucleases BglII and EagI and the C3d encoding fragments purified from a 1% (w/v) agarose gel. PBC00-02 is similarly cut with BglII and EagI and the larger fragment (vector fragment) purified form a 0.9% (w/v) agarose gel.

The vector fragments and the C3d encoding fragments are ligated and transformed into *E. coli* XL-1 blue under standard condition and the clones isolated and screened by restriction mapping. The new plasmids are designated: pBC68-10 to 19 encoding one fuzzy C3d domain and pBC68-20 to 29 encoding one fuzzy C3d variant and the native C3d sequence and pBC68 30-39 containing two fuzzy C3d variant and a native the C3d sequence.

Example 5

Construction a Baculovirus Vector and Expression of a Cysteine-tailed C3d Monomer in Insect Cells (a) Construction of pBP66-06

The C-terminal cysteine was introduced by site direct mutagenesis of the plasmid pBP66-01 to form pBP66-06. This plasmid was subjected to site directed mutagenesis with oligonucleotides with the following sequence: CCAG-CAGTGGATCCTGCTAGAGTTCTGAGG (Seq ID 33) and CCTCAGAACTCTAGCAGGATCCACTGCTGG (Seq ID 34). Site directed mutagenesis was carried out using a "QuickChange" kit obtained from Stratagene (Cambridge UK.) according to the manufacturer's protocols. The resulting plasmid, pBP66-06 was transformed into competent $E.$ $coli$ XL1-blue purchased from Stratagene. Ampicillin resistant transformants were selected on LB-agar plates containing 50 µg/ml ampicillin. Plasmid DNA extracted from the resulting colonies is identified initially by restriction enzyme digest and confirmed by DNA sequencing.

(b) Expression of Cysteine-tailed C3d Sequence in Baculovirus/Sf9 System

Recombinant baculoviruses were generated from the plasmids constructed as described in Section (a), this example and used to express the encoded polypeptide according to the methods described in "General Methodology used in examples" Sections (viii) to (x).

(c) Purification and Characterisation or the Cysteine-tailed C3d in Sf9/Baculovirus System The (C3d)-cys tailed protein is purified as described in Section (xiv) of General Methods, characterised biologically by the methods described in Section (xvii) and physically characterised as described in (xv) and (xvi) (b–c).

(d) Conjugation of C3d-cys or(C3d)3-cys with Antigen

Purified $C3d_n$-cys is treated with Tris (2-carboxyethyl) phosphine.HCl (TCEP) to remove any blocking moiety on the C-terminal cysteine. Thus, $C3d_n$ (10 µM; 1 ml) is mixed with TCEP (5 mM in 50 mM Hepes pH 4.5; 0.008 ml) and incubated at 20 to 25° C. for about 18 h to give solution A. Antigen is prepared typically by chemical attachment of a suitable linking group to the antigen followed by conjugation to the free cysteine on the (C3d)3 molecule. Antigen (20 µM in 0.1M Trien pH 8.0; 1.0 ml) is mixed wit 2-iminothiolane (10 mM in 0.1M Trien pH 8.0; 0.01 ml) and incubated at 20 to 25° C. for 1 h DTNB (100 mM in 0.1M Trien pH 8.0; 0.01 ml) is added and the mixture left for a further 1 h. The mixture is then buffer exchanged into 0.1M Trien pH 8.0 (2.0 ml) using Sephadex G25 (PD10; Pharmacia) to give solution B. Solution B (1.0 ml) is mixed with solution A (1.0 ml) and incubated at 20 to 25° C. for 18 h optionally with concentration by ultrafiltration to give solution C. Solution C is optionally purified to remove unreacted materials, for example by size exclusion chromatography, and then formulated into final product. This formulation may involve buffer-exchange into a physiologically acceptable buffer, for example phosphate buffered saline, followed by sterile filtration, aliquoting and freezing or it may involve buffer-exchange into a suitable buffer for lyophilisation.

Example 6

Construction a Baculovirus Vector and Expression of a Cysteine-tailed C3d3 Insect Cells a) Construction of pBP66-08 pBP66-08 was derived from pBP66-06 (see example 5), which is a baculovirus transfer vector containing a single copy of G3d-cys. A unique KpnI restriction site was engineered into the vector between the signal peptide and the C3d coding sequence to allow insertion of additional copies of the C3d sequence in which the additional copies of C3d differ from the original C3d sequence, and from each other by approximately 10% or more, but encode a polypeptide which is identical between residues $Thr_1$ and $Pro_{295}$ but may encode a linker or spacer sequence, such as the polypeptide sequence Ser-Ser-Gly-Ser-Gly-Gly-Gly-Gly-Ser-Gly-Gly-Gly-Gly-Ser-Gly-Ser (SEQ ID NO: 48), such as the fuzzy C3d monomer genes obtained using methods described in example 3.

In order to introduce the KpnI site pBP66-06 was subjected to site directed mutagenesis with oligonucleotides with the following sequence: CCACCCGAGCCGGTAC-CAGATCTA (Seq ID 41) and GGTAGATCTGGTACCG-GCTCGGGTGG (Seq ID 42). Site directed mutagenesis was carried out using a "QuickChange" kit obtained from Stratagene (Cambridge UK.) according to the manufacturer's protocols. The resulting plasmid, pBP66-08 was transformed into competent $E.$ $coli$ XL1-blue purchased from Stratagene. Ampicillin resistant transformants were selected on LB-agar plates containing 50 µg/ml ampicillin. Plasmid DNA extracted from the resulting colonies is identified initially by restriction enzyme digest and confirmed by DNA sequencing.

Construction of pBP67-08 and pBP68-08 pBP67-08 contains an additional copy of C3d with variant sequence inserted at the KpnI site of pBP66-08, pBP66-08 contains two additional copies of C3d with variant sequence inserted at the KpnI site of pBP66-08. The sequence of the additional copies of C3d differ from the original C3d sequence, and from each other by approximately 10% or more, but encode a polypeptide which is identical between residues ThrI and Pro 295, but may encode a linker or spacer sequence, such as the polypeptide sequence Ser-Ser-Gly-Ser-Gly-Gly-Gly-Gly-Ser-Gly-Gly-Gly-Gly-Ser-Gly-Ser (SEQ ID NO: 48). C3d monomers obtained using the methods described in example 3 are engineered to be inserted at the KpnI site by PCR amplification with the following primer pair: CGAGCCATATGGGTACCAC-CCCAGC (SEQ ID NO: 43) and GGTTAGCAGGTACCG-GAACC (SEQ ID NO: 44) followed by digestion of the PCR product with the restriction enzyme KpnI.

The vector pBP66-08 is digested with XpnI and, to inhibit self-ligation of the vector, is then incubated with shrimp alkaline phosphatase (Amersham Life Sciences Inc) according to the manufacturer's instructions. The resultant fragment is ligated with the KpnI digested PCR products which may encode a single variant sequence of C3d or a mixture of more than one variant sequence of C3d. The ligated DNAs are transformed into competent $E.$ $coli$ XL1-blue purchased from Stratagene. Ampicillin resistant transformants were selected on LB-agar plates containing 50 µg/ml ampicillin. Plasmid DNA extracted from the resulting colonies is identified initially by restriction enzyme digest to identify correctly oriented insertions of one or two variant copies of C3d and confirmed by DNA sequencing.

(b) Expression or Cysteine-tailed $C3d_2$ or Cysteine-tailed $C3d_3$ Sequence in Baculovirus/Sf9 System Recombinant baculoviruses were generated from the plasmids constructed as described in Section (a), this example, and used to express the encoded polypeptide according to the methods described in "General Methodology used in examples" Sections (viii) to (x).
(c) Purification and Characterisation of the Cysteine-tailed $C3d_2$ or Cysteine-tailed $C3d_3$ in Sf9/baculovirus System The $C3d_n$-cys tailed protein is purified as described in Section (xiv) of General Methods, characterised biologically by the methods described in Section (xvii) and physically characterised as described in (xv) and (xvi) (b–c).

Example 7

Construction a Bacterial Vector and Expression of a Cysteine-tailed C3d Monomer in E. coli (A) Construction of pBC66-06

The C-terminal cysteine was introduced by site direct mutagenesis of the plasmid pDB-1033 to form pBC66-06. This plasmid was subjected to site directed mutagenesis with oligonucleotides with the following sequence: GGATCT GAAGAGTTCTGCTGAGGATCCTATTAAAGC(Seq ID 45) and GCTTTAATAGGATCCTCAGCAGAACTCT- TCAGATCC (Seq ID 46). Site directed mutagenesis was carried out using a "QuickChange" kit obtained from Stratagene (Cambridge UK.) according to the manufacturer's protocols. The resulting plasmid, pBC66-06 was transformed into competent E. coli XL1-blue purchased from Statagene. Ampicillin resistant transformants were selected on LB-agar plates containing 50 µg/ml ampicillin. Plasmid DNA extracted from the resulting colonies was identified initially by restriction enzyme digest and confirmed by DNA sequencing. The amino acid sequence for the C3d1-cys construct is given in Sequence ID 26,
(b) Expression of C3d1-cys from pBC66-06 pBC66-06 was transformed into calcium chloride competent E. coli BL21(DE3) and resultant colonies were isolated and checked for plasmid content. To express protein from pBC66-06 in E. coli BL21(DE3), a single colony was inoculated into 10 ml LB media (20 g/l tryptone, 15 g/l yeast extract, 0.8 g/l NaCl, 0.2 g/l $Na_2HPO_4$, 0.1 g/l $KH_2PO_4$) containing 50 µg/ml ampicillin (Sigma). The culture was grown for 6 hours at 37° C., 260 rpm before being used to inoculate 250 ml of the same media containing 50 µg/ml ampicillin, growth was under the same conditions overnight. 20 ml of the overnight culture was then used to inoculate each 5×1000 ml of the LB with 50 µg/ml ampicillin in 5l Erienmeyer flask. Cells were grown to an OD of about 0.6 at $A_{550}$ nm at 37° C., 200 rpm. To induce expression of the protein 1PTG (isopropyl β-D galactopyranoside) was added to a final concentration of 1 mM and cells incubated at 20° C., 200 rpm for about 16 hours before harvesting the cells by centrifugation at 3000 g/25 minutes. The cell pellet from 5l of culture was processed immediately.
(c) Purification of (C3d)1-cys
(f) Isolation of Soluble C3d1-cys The cell pellet of E. coli BL21(DE3) (pBC66-06) was resuspended in approximately 100 ml of 50 mM Tris pH8.0 containing 0.1MNaCl, 10 mM EDTA, 10 µM 3,4-dichloroisocoumarin and 10 µM L-trans-epoxysuccinyl-leucylamide-(-4-guanidino-)-butane, N-[N-(L-3-transcarboxyirane-2-carbonyl) L-leucyl]-agmatine. The suspension was transferred to a high pressure homogeniser (Emulsiflex C5) cooled to 4° C., and the cells were disrupted by passing the suspension twice through the homogeniser at 12000 PSI. The homogenate was spun at 9000 g for 20 minutes. The supernatant was decanted and stored at −40° C., and the pellet discarded.

(ii) Purification of Soluble C3d1-cys

The soluble homogenate fraction was diluted 1:1 with 50 mM Hepes pH 7.5 and applied to a Macroprep High-Q column (bed volume about 100 ml, Biorad) pre-equilibrated with 50 mM Hepes pH 7.5. The column was eluted with a linear NaCl gradient from 0 to 0.35M NaCl over 500 ml. The fractions containing C3d1-cys were assessed by SDS-PAGE and western blotting as described in the general methods section (xv) and (xvib) and pooled for further purification and stored at −40° C.

The C3d 1-cys containing fractions from the Macroprep High-Q purification were diluted 1:1 with 4M ammonium sulphate, 50 mM Hepes pH7.5. This solution was applied to an ether-Toyopearl column (bed volume 25 ml. ToyoHaas) pre-equilibrated in 2M ammonium sulphate, 50 mM Hepes pH7.5 and eluted with a linear gradient to 0M ammonium sulphate. Fractions were assessed for purity by SDS-PAGE and western blotting as described in in the general methods section (xv) and (xvib). Fractions containing C3d-cys were pooled and stored at −40° C.

Prior to application onto the final column the pooled fractions containing the C3d-cys from the ether-Toyopearl column were buffered exchanged by dialysis against an ×500-fold volume excess of 10 mM phosphate buffer pH6.8 containing 1 mM magnesium chloride. The dialysate was applied to a 20 ml bed volume 80 µM Macroprep Ceramic Hydroxyapatite (Type 1, Biorad) pre-equilibrated with 10 mM phosphate buffer pH6.8 containing 1 mM magnesium chloride. The C3d-cys eluted typically in the unbound fractions and in the 5 mM magnesium chloride, 10 mM phosphate buffer eluate, all other impurities bound to the column and were eluted in 0.3M phosphate pH6.8. Fractions were assessed for purity by SDS-PAGE and western blotting as described in in the general methods section (xv) and (xvib). Fractions containing C3d-cys at greater than 90% purity were pooled and stored at −40° C.

Example 8

A trifunctional Linker Reagent for Coupling C3dcys and (C3d)n-cys to Antigens
N-Acetyl-Lys(N-ε-PDP)-Ala-Lys(N-ε-PDP)-Ala-Lys(N-ε-PDP)-OH (SEQ ID NO: 49) (PDP=3=(2-pyridyldithio) propionyl, all-L).

The peptide Ala-Lys-Ala-Lys-Ala-Lys (SEQ ID NO: 40) was prepared using solid phase synthesis via the general Fmoc/tBu strategy developed by Sheppard and Atherton (E. Atherton and R. C. Sheppard, Solid Phase Synthesis IRL Press, Oxford, 1989). Kieselguhr-supported polydimethylacrylamide resin (Macrosorb 100) was used as the solid support and was derivatised with ethylene diamine. Coupling reactions were carried out using N-α-Fmoc protected reagents pre-reactivated with N,N'-diisopropylcarbodiimide/N-hydroxybenzotriazole (in 4-fold molar excess) with bromophenol blue monitoring. Fmoc cleavages used 20% piperidine in DMF. Reactions to assemble the peptide chain were carried out by repeated cycles of coupling and deprotection. Lysine was protected with the t-Boc grouping.

On completion of the peptide assembly and with the peptide still attached to the resin, the acetyl group was attached to the amino group of the N terminal glycine by treatment with acetic anhydride. This modified peptide was then cleaved from the resin and the side-chain protecting groups removed at the same time by treatment with trifluoracetic acid containing 2.5% water and 2.5% triisopropyl silane. The product was neutralised, dried reacted with a 3.3 molar excess of 3-(2-pyridyldithio)propionic acid N-oxysuccinimide ester and then purified by reverse-phase high performance liquid chromatography using a gradient of 0.1% trifluoroacetic acid in water with 0.1% trifluoroacetic acid in acetonitrile. The product was approximately 92% pure. Fast atom bombardment mass spectrometry gave a molecular ion of 1178.4 Daltons (calculated: 1177.2) and a monosodiated ion of 1200.4 Daltons.

This peptide was converted into a active ester form for protein derivatisation as follows. Peptide (20 mg) was dissolved in dry N,N dimethylformamide (0.5 ml) at room temperature and N,N' dicyclohexylcarbodiimide added (4.5 mg). The solution was allowed to react at room temperature for 15 min and the precipitate removed by filtration. N-Hydroxysulphosuccinimide (4.5 mg, 1 equivalent) was added and the solution allowed to react at room temperature overnight. The solvent was removed by vacuum evaporation to give a white solid which was stored desiccated at −40° C.

Example 9

Chemical Coupling of C3dcys and $C3d_n$ cys to Antigen Using a Coupled Thiolation Reaction Antigens may conveniently be derivatised for further reaction with polypeptides containing a free cysteine by raction with 2-iminothioane in the presence of an excess of a reactive disulphide such as 2.2' dithiobis-(5-nitrobenzoic acid) [DTNB] as noted above.

A recombinant 19 kDa fragment of merozoite surface protein-1 (MSP-1/19) [200 μl of 4.32 mg/ml in 0.05M sodium phosphate 0.1M sodium chloride pH.7.4, PBS) was mixed with 0.1M triethanolamine hydrochloride pH 8.0, 0.5 ml followed by 50 μl of 100 mM DTNB in dimethylsulphoxide and 20 μl of 100 mM 2-iminothiolane freshly made up in water. The mixture was incubated at 25° C. for 90 min. The product was gel filtered into PBS (2.0 ml) at 4° C. using a disposable Sephadex G-25 column. An aliquot of this material was reduced using 2 mM L-cysteine and from the optical density change at 412 nm the degree of substitution by activated disulphides was estimated at approximately 2.3 moles of mixed DTNB/3-thiopropamidine disuhphide per mole of protein.

This material is mixed with an approximately 3-fold molar excess of C3dcys an concentrated using a Centricon-10 centrifugal concentrator with a ~10 kDa molecular weight cut-off to ~20% of its original volume. The product is then applied to a Sepahadex G-100 gel permeation chromatography column and products eluting at or near the excluded volume are collected. Materials with a molecular weight of <~50 kDa are unmodified starting materials or mono-conjugate with C3d-cys and are discarded.

Example 10

Chemical Coupling of C3cys and $C3d_n$cys to Antigen Using a Trifunctional Coupling Reagent The active ester derivative of the peptide of Example 8 is dissolved to a concentration of approximately 2 mM in dry dimethylsulphoxide and added to a solution of MSP-1/19 (approximatel 0.2 mM in PBS) to a final concentration of 0.2 mM. The product is incubated for 1 h at 25° C., and then chromatographed on a small gel filtration colun as described in Example 9. This product is then mixed with C3dcys and concentrated and purified by fractionation on Sepahadex G-100 as described above.

Example 11

Construction of a Vector for Expression of a Malaria Antigen Fused to $C3d_3$

The 19 kDa protein derived from the C terminus of the merozoite safe protein (MSP-1) of malaria parasites of the Plasmodium species may be used as an immunogen against malaria infection. *Plasmodium yoelii* (mouse malaria) is used as a model for the human disease. A plasmid is constructed containing three copies of C3d fed to the gene encoding the 19 kDa Carboxy-terminal fragment of *P. yoelii* MSP-1(MSP1$_{19}$) (amino acids His$_{1419}$ to Ser$_{1754}$ of *P. yoelii*). DNA encoding MSP1$_1$ is obtained from the plasmid bGST-MSP1(19) (Tian et al., 1996 J. Immunology 157, 1176–1183). PCR primers are designed to amplify the MSP1$_{19}$ gene with appropriate flanking restriction sites to allow in-frame fusion of MSP1$_{19}$ to either the amino terminus of the first copy of C3d or the carboxy terminus of the third copy of C3d.

Example 12

Expression and Purification of C3d Oligomers as Intein Fusion Proteins (a) Construction of pBP81-01 and pBP83-01

In this example, a form of C3d or C3d oligomers is expressed with a carboxy terminal reactive thiolester allowing direct covalent coupling to the antigen of choice. It should be noted the natural C3d sequence normally contains a thiolester that is buried in native C3 and is the site of attachment to antigen in C3b and its fragments. In the plasmid pSG.C3d$_1$. YL and its derivatives the cysteine residue that is the biosynthetic precursor of the natural thiolester is mutated to prevent interference with disulphide bond formation in recombinant C3d proteins (Dempsey et al, Science 271, 348–350, 1996). In the present construct the thiolester is effectively moved to the C-terminus of the C3d domain.

The carboxy terminal of C3d in the vector pBP66-01 or any of the pBP68-20 to pBP68-29 series is modified by site directed mutagenesis to introduce novel restriction sites SapI and PstI using of oligonucleotides #50391 (Seq ID No 35) (CCAGCAGTGGCTCTTCCTGCTTCTG CAGGATC) and #50392 (Seq ID No 36) (GATCCTGCAGAAGCAGGAAGAGCCACT GCTGG). Site directed mutagenesis is carried out using a "Quick-Change" kit obtained from Stratagene according to the manufacturer's protocols. The resulting plasmids, pBP60-07 and pBP68-50 to pBP68-59 are transformed into competent *E. coli* XL1-blue purchased from Stratagene. Ampicillin resistant transformants are selected on LB-agar plates containing 50 μg/ml ampicillin, Plasmid DNA extracted from the resulting colonies is identified initially by restriction enzyme digest and confirmed by DNA sequencing.

b) Construction of pBP66-07 and pBP68-60 to pBP68-69 pBP81-01 and pBP83-50 to pBP83-59 are plasmids in which the genes for intein and the chitin binding domain are cloned in frame downstream of the C3d-wild type or (C3d)3 in which one or more of the domains is fuzzy to prevent homologous recombination. The intein and chitin binding domain sequences art obtained from the commercially available plasmid pCYB1 (New England Biolabs) by digestion with the enzymes SapI and PsiI and purification of the 1560 base pair fragment, this is termed fragment 1. pBP66-07 and pBP68-50 to pBP68-59 are digested with SapI and PstI and a fragment of 6718 base pairs is purified from pBP66-07 (Fragment 2) and a fragment of 8590 base pain is purified from pBP68-50 to pBP68-59 (fragments 3a–3j).

Fragments 1 and 2 are ligated using T4 DNA ligase to give pBP81-01. Fragments 3 a to 3j fragments are each ligated with fragment 1 using T4 DNA ligase to give pBP83-50 to pBP83-59. The ligated plasmids are transformed in competent *E. coli* XL1-blue purchased from Stratagene. Ampicillin resistant transformants are selected on LB-agar plates containing 50 µg/ml ampicillin. Plasmid DNA extracted from the resulting colonies is analysed by restriction endonuclease digestion and confirmed by DNA sequencing.

(c) Expression of C3d Oligomers Fused to Intein and Chitin Binding Protein

Recombinant baculoviruses are generated from the plasmids constructed as described in Section b) (this example) and used to express the encoded polypeptide according to the methods described in "General Methodology used in examples" Sections (viii) to (x).

(d) Purification and Cleavage of $C3d_n$-intein Fusion Proteins to Generate Carboxy Terminal Reactive Thiolester The $C3d_n$-intein-chitin binding domain fusion protein is purified from material expressed into the media by the Sf9 infected baculovirus cells. Prior to loading onto the chitin bead affinity column (New England Biolabs, Herts) the pH of the media is corrected to pH 8.0 by addition of 10M NaOH. The salt concentration of the media is measured by conductivity, usually about 0.08M and solid NaCl added to the media to give a final concentration of 0.5M NaCl.

The $C3d_n$-intein-chitin binding domain fusion containing supernatant is loaded onto the chitin bead affinity matrix column and separation carried out according to the instructions in the 'IMPACT I' kit (New England Biolabs, Herts, UK). The cleavage on the column utilises a protein splicing mechanism known as an intein and this undergoes a self cleavage reaction between the C-terminal of the $C3d_n$ and the N-terminal of the intein in the presence of a reducing agent e.g. DTT. As a result of this reaction the eluted $C3d_n$ contains a reactive thiolester at its C-terminal. The resulting affinity purified protein should be at least 90% pure, if the purity is less than 90% prior to coupling to antigen it should be further purified using techniques described in General Methods Section (xiv).

(e) Reaction with C3d(n)-thioester with Antigen.

The activated thiolester produced by the cleavage at the C-terminal of $C3d_n$ by the intein mechanism (Section d above) can be used to couple antigen to the molecule. The thiolester will react with free nucleophiles on the surface of the antigen e.g. the amino acid lysine or under some circumstances with hydroxyl groups contained in aminoacids such as serine and tyrosine or in the sugar groups of glycosylated proteins. The antigen should be present in at least a ten-fold molar excess to that of the thiolester and is preferably added to the purified (C3d)n after elution from the column and during processing to remove the DTT (which acts as a competing nucleophile) and to co-concentrate the proteins. The formation of the antigen-C3d can be monitored by mass spectrometry and/or gel electrophoresis to detect all the species in the population. The complexes containing at least one C3d and one antigen unit can be separated for instance by gel filtration of by separation through a size exclusion membrane that would allow separation of the multimers from the monomers.

Example 13

Construction of a Fuzzy Genes Encoding Species Variants of (C3d)3

All the above examples employed the murine C3d sequence. Using methodology described in Example 3, fuzzy C3d sequences can be devised for any species including but not restricted to human, cat, rabbit, bovine, ovine, equine and goat to generate a series of variants containing either a single C3d domain, or two independent fuzzy variant domains of C3d and a single domain of invariant DNA sequence. Subsequent modifications described in all later Examples can be carried out in an identical manner.

Where the sequence is known e.g. human (de Bruin and Fey (1985) PNAS(USA) 82:708–712) the Fuzzy oligonucleotides can be generated directly; in cases where the sequence is unknown C3d hybridisation probes from either the human or mouse can be used to identify and therefore clone and sequence C3d from the chosen species library.

This application claims priority to GB 9727512.7, filed Dec. 31, 1997, which is hereby incorporated by reference.

APPENDIX
Sequence Data

```
Seq ID No 1:DNA sequence of Fuz1
CACCCGAGCCATATGAGATCTACNCCWGCNGGNTCHGGNGARCARAAYATGATYGGNATG
ACNCCWACNGTNATYGCNGTNCACTACCTGGACCAGACCG Seq ID No 2:DNA sequence of Fuz2
GGCCAGCTGCTGGGTRTANCCYTTYTTRATVAGYTCVAGNGCYTCYTGRCGYTTYTCRAT
NCCRAAYTTYTCCCAYTGYTCGGTCTGGTCCAGG Seq ID No 3:DNA sequence of Fuz3
CCCAGCAGCTGGCCTTYAARCARCCWTCHTCHGCNTAYGCNGCNTTYAAYAAYCGYCCWC
CWTCHACNTGGCTBACNGCCTACGTGGTCAAGG Seq ID No 4:DNA sequence of Fuz4
CCGGCTTCTGCTTCTCCAGRATVAGCCAYTTNACNGCNCCRCAVAGNACGTGDGARTCRA
TNGCRATVAGRTTNGCNGCVAGDGARAANACCTTGACCACGTAGGC Seq ID No 5:DNA sequence of Fuz5
GGAGAAGCAGAAGCCGGAYGGNGTNTTYCARGARGAYGGNCCWGTNATYCACCARGARAT
GATYGGNGGNTTYCGNAACGCCAAGGAGGCAGATG Seq ID No 6:DNA sequence of Fuz6
GCTCCCAGGAAGGCTRTTNACYTGNCCYTCRCARATRTCRCGNGCYTCYTGVAGNGCAAT
VAGNACRAANGCNGTVAGDGANACATCTGCCTCCTTGGCG Seq ID No 7:DNA sequence of Fuz7
GCCTTCCTGGGAGCATYAAYAARGCNGGNGARTAYATYGARGCNTCHTAYATGAAYCTBC
```

APPENDIX
Sequence Data

ARCGYCCWTAYACNGTNGCNATYGCNGGGTATGCCCTGGCC

Seq ID No 8:DNA sequence of Fuz8
CTGGTCAGGCTCCTCCCARCGRTTRCGRTCYTTNGCNGTRTTVAGRAAYTTNCCNAGRTA
WGGYTCYTCVAGYTTRTTCATVAGGGCCAGGGCATACCC Seq ID No 9:DNA sequence of Fuz9
GAGGAGCCTGACCAGCARCTBTAYAAYGTNGARGCNACNTCHTAYGCNCTBCTBGCNCTB
CTBCTBCTBAARGAYTTYGAYTCHGTGCCCCCTGTAGTGC Seq ID No 10:DNA sequence of Fuz10
GGGCCAAGGCTTGGAANACCATRAANGTNGCYTGNGTDGANCCRTANCCNCCNCCRTART
ARCGYTGYTCRTTVAGCCANCGCACTACAGGGGGC Seq ID No 11:DNA sequence of Fuz11
CCAAGCCTTGGCCCARTAYCARACNGAYGTNCCAGAYCACAARGAYCTNAAYATGGAYGT
NTCCTTCCACCTCCCC Seq ID No 12:DNA sequence of Fuz12
CCCAGAGCCGGCCGGTTATCAGGATCCDGANCCNCCNCCNCCDGANCCNCCNCCNCCDGA
NCCDGADGAGGGGAGGTGGAAGG Seq ID No 13:DNA sequence of Fuz13
GGCTGATTCTCGAGAAGCAGAAGC Seq ID No 14:DNA sequence oF Fuz14
GCTTCTGCTTCTCGAGAATCAGCC Seq ID No 15:DNA sequence of Fuz15
GCCTTCCCGGGAGCATCAACAAGGC Seq ID No 16:DNA sequence of Fuz16
GCCTTGTTGACGCTCCCGGGAAGGC Seq ID No 17:DNA sequence of Fuz17
GGAGCCTGATCAGCAGCTCTACAACG Seq ID No 18:DNA sequence of Fuz18
CGTTGTAGAGCTGCTGATCAGGCTCC Seq ID No 19:DNA sequence of Fuz19
GGGTACACCCAGCAGCTGGCC Seq ID No 20:DNA sequence of Fuz20
GGCCAGCTGCTGGGTGTACCC Seq ID No 21:DNA sequence of Fuz21
GGTGTTCCAAGCTTTGGCCC Seq ID No 22:DNA sequence of Fuz22
GGGCCAAAGCTTGGAACACC Seq ID No 23:DNA sequence of Fuz23
CACCCGAGCCATATGAG Seq ID No 24:DNA sequence of Fuz24
CCCAGAGCCGGCCGGTTATCAGGATCC SEQ ID No 25:DNA sequence of Fuz25
CCCAGAGCCGGCCGGTTAGCAGGATCC SEQ ID No 26
C3dlcys amino acid sequence expressed in *E. coli*
```
 1  Met Ala Ser Gly Ser Thr Pro Ala Gly Ser 11  Gly Glu Gln Asn Met Ile Gly Met Thr Pro 21  Thr Val Ile Ala Val His Tyr Leu Asp Gln 31  Thr Glu Gln Trp Glu Lys Phe Gly Ile Glu 41  Lys Arg Gln Glu Ala Leu Glu Leu Ile Lys 51  Lys Gly Tyr Thr Gln Gln Leu Ala Phe Lys 61  Gln Pro Ser Ser Ala Tyr Ala Ala Phe Asn
```

-continued

APPENDIX
Sequence Data

```
 71  Asn Arg Pro Pro Ser Thr Trp Leu Thr Ala

81  Tyr Val Val Lys Val Phe Ser Leu Ala Ala

91  Gln Leu Ile Ala Ile Asp Ser His Val Leu

101  Cys Gly Ala Val Lys Trp Leu Ile Leu Glu

111  Lys Gln Lys Pro Asp Gly Val Phe Gln Glu

121  Asp Gly Pro Val Ile His Gln Glu Met Ile

131  Gly Gly Phe Arg Asn Ala Lys Glu Ala Asp

141  Val Ser Leu Thr Ala Phe Val Leu Ile Ala

151  Leu Gln Glu Ala Arg Asp Ile Cys Glu Gly

161  Gln Val Asn Ser Leu Pro Gly Ser Ile Asn

171  Lys Ala Gly Glu Tyr Ile Glu Ala Ser Tyr

181  Met Asn Leu Gln Arg Pro Tyr Thr Val Ala

191  Ile Ala Gly Tyr Ala Leu Ala Leu Met Asn

201  Lys Leu Glu Glu Pro Tyr Leu Gly Lys Phe

211  Leu Asn Thr Ala Lys Asp Arg Asn Arg Trp

221  Glu Glu Pro Asp Gln Gln Leu Tyr Asn Val

231  Glu Ala Thr Ser Tyr Ala Leu Leu Ala Leu

241  Leu Leu Leu Lys Asp Phe Asp Ser Val Pro

251  Pro Val Val Arg Trp Leu Asn Glu Gln Arg

261  Tyr Tyr Gly Gly Gly Tyr Gly Ser Thr Gln

271  Ala Thr Phe Met Val Phe Gln Ala Leu Ala

281  Gln Tyr Gln Thr Asp Val Pro Asp His Asp

291  Leu Asn Met Asp Val Ser Phe His Leu Pro

301  Ser Ser Gly Ser Glu Glu Phe Cys
```

SEQ ID No 27
(C3d)3 amino acid sequence expressed in *E. coli*

```
  1  Met Ala Ser Gly Ser Thr Pro Ala Gly Ser

11  Gly Glu Gln Asn Met Ile Gly Met Thr Pro

21  Thr Val Ile Ala Val His Tyr Leu Asp Gln

31  Thr Glu Gln Trp Glu Lys Phe Gly Ile Glu

41  Lys Arg Gln Glu Ala Leu Glu Leu Ile Lys

52  Lys Gly Tyr Thr Gln Gln Leu Ala Phe Lys

62  Gln Pro Ser Ser Ala Tyr Ala Ala Phe Asn

72  Asn Arg Pro Pro Ser Thr Trp Leu Thr Ala

82  Tyr Val Val Lys Val Phe Ser Leu Ala Ala

91  Gln Leu Ile Ala Ile Asp Ser His Val Leu

102  Cys Gly Ala Val Lys Trp Leu Ile Leu Glu

112  Lys Gln Lys Pro Asp Gly Val Phe Gln Glu

122  Asp Gly Pro Val Ile His Gln Glu Met Ile
```

-continued

APPENDIX
Sequence Data

```
132  Gly Gly Phe Arg Asn Ala Lys Glu Ala Asp
141  Val Ser Leu Thr Ala Phe Val Leu Ile Ala
152  Leu Gln Glu Ala Arg Asp Ile Cys Glu Gly
162  Gln Val Asn Ser Leu Pro Gly Ser Ile Asn
172  Lys Ala Gly Glu Tyr Ile Glu Ala Ser Tyr
182  Met Asn Leu Gln Arg Pro Tyr Thr Val Ala
191  Ile Ala Gly Tyr Ala Leu Ala Leu Met Asn
202  Lys Leu Glu Glu Pro Tyr Leu Gly Lys Phe
212  Leu Asn Thr Ala Lys Asp Arg Asn Arg Trp
222  Glu Glu Pro Asp Gln Gln Leu Tyr Asn Val
232  Glu Ala Thr Ser Tyr Ala Leu Leu Ala Leu
241  Leu Leu Leu Lys Asp Phe Asp Ser Val Pro
252  Pro Val Val Arg Trp Leu Asn Glu Gln Arg
262  Tyr Tyr Gly Gly Gly Tyr Gly Ser Thr Gln
272  Ala Thr Phe Met Val Phe Gln Ala Leu Ala
282  Gln Tyr Gln Thr Asp Val Pro Asp His Asp
292  Leu Asn Met Asp Val Ser Phe His Leu Pro
301  Ser Ser Gly Ser Gly Gly Gly Gly Ser Gly
311  Gly Gly Gly Ser Gly Ser Thr Pro Ala Gly
321  Ser Gly Glu Gln Asn Met Ile Gly Met Thr
331  Pro Thr Val Ile Ala Val His Tyr Leu Asp
341  Gln Thr Glu Gln Trp Glu Lys Phe Gly Ile
351  Glu Lys Arg Gln Glu Ala Leu Glu Leu Ile
361  Lys Lys Gly Tyr Thr Gln Gln Ile Ala Phe
371  Lys Gln Pro Ser Ser Ala Tyr Ala Ala Phe
381  Asn Asn Arg Pro Pro Ser Thr Trp Leu Thr
391  Ala Tyr Val Val Lys Val Phe Ser Leu Ala
401  Ala Gln Leu Ile Ala Ile Asp Ser His Val
411  Ile Cys Gly Ala Val Lys Trp Leu Ile Leu
421  Glu Lys Gln Lys Pro Asp Gly Val Phe Gln
431  Glu Asp Gly Pro Val Ile His Gln Glu Met
441  Ile Gly Gly Phe Arg Asn Ala Lys Glu Ala
451  Asp Val Ser Leu Thr Ala Phe Val Leu Ile
461  Ala Leu Gln Glu Ala Arg Asp Ile Cys Glu
471  Gly Gln Val Asn Ser Leu Pro Gly Ser Ile
481  Asn Lys Ala Gly Glu Tyr Ile Glu Ala Ser
491  Tyr Met Asn Leu Gln Arg Pro Tyr Thr Val
501  Ala Ile Ala Gly Tyr Ala Leu Ala Leu Met
```

-continued

APPENDIX
Sequence Data

511 Asn Lys Leu Glu Glu Pro Tyr Leu Gly Lys

521 Phe Leu Asn Thr Ala Lys Asp Arg Asn Arg

531 Trp Glu Glu Pro Asp Gln Gln Leu Tyr Asn

541 Val Glu Ala Thr Ser Tyr Ala Leu Leu Ala

551 Leu Leu Leu Leu Lys Asp Phe Asp Ser Val

561 Pro Pro Val Val Arg Trp Leu Asn Glu Gln

571 Arg Tyr Tyr Gly Gly Gly Thr Gly Ser Thr

581 Gln Ala Thr Phe Met Val Phe Gln Ala Leu

591 Ala Gln Tyr Gln Thr Asp Val Pro Asp His

601 Asp Leu Asn Met Asp Val Ser Phe His Leu

611 Pro Ser Ser Gly Ser Gly Gly Gly Gly Ser

621 Gly Gly Gly Gly Ser Gly Ser Thr Pro Ala

631 Gly Ser Gly Glu Gln Asn Met Ile Gly Met

641 Thr Pro Thr Val Ile Ala Val His Tyr Leu

651 Asp Gln Thr Glu Gln Trp Glu Lys Phe Gly

661 Ile Gln Lys Arg Gln Glu Ala Leu Glu Leu

671 Ile Lys Lys Gly Tyr Thr Gln Gln Leu Ala

681 Phe Lys Gln Pro Ser Ser Ala Tyr Ala Ala

691 Pne Asn Asn Arg Pro Pro Ser Thr Trp Leu

701 Thr Ala Tyr Val Val Lys Val Phe Ser Leu

711 Ala Ala Gln Leu Ile Ala Ile Asp Ser His

721 Val Leu Cys Gly Ala Val Lys Trp Leu Ile

731 Leu Glu Lys Gln Lys Asp Gly Val Val Phe

741 Gln Glu Asp Gly Pro Val Ile His Gln Glu

751 Met Ile Gly Gly Phe Arg Asn Ala Lys Glu

761 Ala Asp Val Ser Leu Thr Ala Phe Val Leu

771 Ile Ala Leu Gln Glu Ala Arg Asp Ile Cys

781 Glu Gly Gln Val Asn Ser Ile Pro Gly Ser

791 Ile Asn Lys Ala Gly Glu Tyr Ile Glu Ala

801 Ser Tyr Met Asn Leu Gln Arg Pro Tyr Thr

811 Val Ala Ile Ala Gly Tyr Ala Leu Ala Leu

821 Met Asn Lys Leu Glu Glu Pro Tyr Leu Gly

831 Lys Phe Leu Asn Thr Ala Lys Asp Arg Asn

841 Arg Trp Glu Glu Pro Asp Gln Gln Leu Tyr

851 Asn Val Glu Ala Thr Ser Tyr Ala Leu Leu

861 Ala Leu Leu Leu Leu Lys Asp Phe Asp Ser

871 Val Pro Pro Val Val Arg Trp Leu Asn Glu

881 Gln Arg Tyr Tyr Gly Gly Gly Tyr Gly Ser

---
APPENDIX
Sequence Data
---

891  Thr Gln Ala Thr Phe Met Val Phe Gln Ala

901  Leu Ala Gln Tyr Gln Thr Asp Val Pro Asp

911  His Asp Leu Asn Met Asp Val Ser Phe His

921  Leu Pro Ser Ser Gly Ser Glu Glu Phe

SEQ. ID No 28
TATGGGTAGCG

SEQ. ID No 29
ACCGATCGCCTAG

Seq ID No 30:DNA sequence of PCR foward primer
GAATTCCTAGCTTGCTTG

Seq ID No 31:DNA sequence of PCR reverse primer
TCTAGAGTCGACCAGAC

Seq ID No 32 DNA sequence of pBC66-01

1  AAATCAATCT AAAGTATATA TGAGTAAACT TGGTCTGACA GTTACCAATG  50
   51  CTTAATCAGT GAGGCACCTA TCTCAGCGAT CTGTCTATTT CGTTCATCCA 100
  101  TAGTTGCCTG ACTCCCCGTC GTGTAGATAA CTACGATACG GGAGGGCTTA 150
  151  CCATCTGGCC CCAGTGCTGC AATGATACCG CGAGACCCAC GCTCACCGGC 200
  201  TCCAGATTTA TCAGCAATAA ACCAGCCAGC CGGAAGGGCC GAGCGCAGAA 250
  251  GTGGTCCTGC AACTTTATCC GCCTCCATCC AGTCTATTAA TTGTTGCCGG 300
  301  GAAGCTAGAG TAAGTAGTTC GCCAGTTAAT AGTTTGCGCA ACGTTGTTGC 350
  351  CATTGCTACA GGCATCGTGG TGTCACGCTC GTCGTTTGGT ATGGCTTCAT 400
  401  TCAGCTCCGG TTCCCAACGA TCAAGGCGAG TTACATGATC CCCCATGTTG 450
  451  TGCAAAAAAG CGGTTAGCTC CTTCGGTCCT CCGATCGTTG TCAGAAGTAA 500
  501  GTTGGCCGCA GTGTTATCAC TCATGGTTAT GGCAGCACTG CATAATTCTC 550
  551  TTACTGTCAT GCCATCCGTA AGATGCTTTT CTGTGACTGG TGAGTACTCA 600
  601  ACCAAGTCAT TCTGAGAATA GTGTATGCGG CGACCGAGTT GCTCTTGCCC 650
  651  GGCGTCAACA CGGGATAATA CCGCGCCACA TAGCAGAACT TTAAAAGTGC 700
  652  TCATCATTGG AAAACGTTCT

TCGGGGCGAAAACTCTCAAGGATCTTACCGCTGTTGAGATCCAGTTCGATGTAACCCACT
CGTGCACCCAACTGATCTTC

AGCATCTTTTACTTTCACCAGCGTTTCTGGGTGAGCAAAAACAGGAAGGCAAAATGCCGC
AAAAAAGGGAATAAGGGCGA

CACGGAAATGTTGAATACTCATACTCTTCCTTTTTCAATATTATTGAAGCATTTATCAGG
GTTATTCTCTCATGAGCGGA

TACATATTTGAATGTATTTAGAAAAATAAACAAATAGGGGTTCCCCGCACATTTCCCCGA
AAAGTGCCACCTGACGTCTA

AGAAACCATTATTATCATGACATTAACCTATAAAAATAGGCGTATCACGAGGCCCTTTCG
TCTTCAAGAATTAAAAGGAT

CTAGGTGAAGATCCTTTTTGATAATCTCATGACCAAAATCCCTTAACGTGAGTTTTCGTT
CCACTGAGCGTCAGACCCCG

TAGAAAAGATCAAAGGATCTTCTTGAGATCCTTTTTTTCTGCGCGTAATCTGCTGCTTGC
AAACAAAAAAACCACCGCTA

CCAGCGGTGGTTTGTTTGCCGGATCAAGAGCTACCAACTCTTTTTCCGAAGGTAACTGGC
TTCAGCAGAGCGCAGATACC

-continued

APPENDIX
Sequence Data

AAATACTGTCCTTCTAGTGTAGCCGTAGTTAGGCCACCACTTCAAGAACTCTGTAGCACC
GCCTACATACCTCGCTCTGC

TAATCCTGTTACCAGTGGCTGCTGCCAGTGGCGATAAGTCGTGTCTTACCGGGTTGGACT
CAAGACGATAGTTACCGGAT

AAGGCGCAGCGGTCGGGCTGAACGGGGGGTTCGTGCACACAGCCCAGCTTGGAGCGAACG
ACCTACACCGAACTGAGATA

CCTACAGCGTGAGCATTGAGAAAGCGCCACGCTTCCCGAAGGGAGAAAGGCGGACAGGTA
TCCGGTAAGCGGCAGGGTCG

GAACAGGAGAGCGCACGAGGGAGCTTCCAGGGGGAAACGCCTGGTATCTTTATAGTCCTG
TCGGGTTTCGCCACCTCTGA

CTTGAGCGTCGATTTTTGTGATGCTCGTCAGGGGGCGGAGCCTATGGAAAAACGCCAGC
AACGCGGCCTTTTTACGGTT

CCTGGCCTTTTGCTGGCCTTTTGCTCACATGTTCTTTCCTGCGTTATCCCCTGATTCTGT
GGATAACCGTATTACCGCCT

TTGAGTGAGCTGATACCGCTCGCCGCAGCCGAACGACCGAGCGCAGCGAGTCAGTGAGCG
AGGAAGCGGAAGAGCGCCTG

ATGCCGTATTTTCTCCTTACGCATCTGTGCGGTATTTCACACCGCATACAGAAAATTAAT
ACGACTCACTATAGGGAGAC

CACAACGGTTTCCCTCTAGAAATAATTTTGTTTAACTTTAAGAAGGAGATATAcatATGg
ctagcggatctaccccgca ggctctggggaacagaacatgattggcatgacaccaacagtcattgcggtacactacctg
gaccagaccgaacagtggga gaagttcggcatagagaagaggcaagaggccctggagctcatcaagaaagggtacaccca
gcagctggccttcaaacagc ccagctctgcctatgctgccttcaacaaccggccccccagcacctggctgacagcctacg
tggtcaaggtcttctctcta gctgccaacctcatcgccatcgactctcacgtcctgtgtgggctgttaaatggttgatt
ctggagaaacagaagccgga tggtgtctttcaggaggatgggcccgtgattcaccaagaaatgattggtggctttcggaa
cgccaaggaggcagatgtgt cactcacagccttcgtcctcatcgcactgcaggaagccagggacatctgtgagggcagg
tcaatagccttcctgggagc atcaacaaggcaggggactatattgaagccagttacatgaacctgcagagaccatacaca
gtggccattgctgggtatgc cctggccctgatgaacaaactggaggaaccttacctcggcaagtttctgaacacagccaa
agatcggaaccgctgggagg agcctgaccagcagctctacaacgtagaggccacatcctacgccctcctggccctgctgc
tgctgaaagactttgactct gtgcccctgtagtgcgctggctcaatgagcaaagatactacggaggcggctatggctcc
acccaggctaccttcatggt attccaagccttggcccaatatcaaacagatgtccctgaccataaggacttgaacatgga
tgtgtccttcracctcccca gcagtggatctgaagagttctgaGGATCTTATTAAAGCAGAACTTGTTTATTGCAGCTTA
TAATGGTTACAAATAAAGCA ATAGCATCACAAATTTCACAAATAAAGCATTTTTTTCACTGCATTCTAGTTGTGGTTTGT
CCAAACTCATCAATGTATCT TATCATGTCTGGTCGACTCTAGAACTAGTAACGACGATCAAGTGGGCATCTGGAGCGGCC
CGGCACCGCAGTGCATCATC CCGAACAAATAATAAAAGCttATCATCGATAAGCTGTCAAACATGAGAATT Seq ID No 33

-continued

APPENDIX
Sequence Data

CCAGCAGTGGATCCTGCTAGAGTTCTGAGG

Seq ID No 34
CCTCAGAACTCTAGCAGGATCCACTGCTGG

Seq ID No 35 DNA sequence of #50391
CCAGCAGTGGCTCTTCCTGCTTCTGCAGGATC

Seq ID No 36 DNA sequence of #50392
GATCCTGCAGAAGCAGGAAGAGCCACTGCTGG

Seq. ID No37 Amino acid sequence of (C3d)3 expressed in baculovirus/Sf9

```
  1  Met Ala Leu Trp Met Arg Leu Leu Pro Leu
 10  Leu Ala Leu Leu Ala Leu Trp Ala Pro ALa
 21  Pro Thr Arg Ala Gly Ser Arg Ser Thr Pro
 31  AIa Gly Ser Gly Glu Gln Asn Met Ile Gly
 41  Met Thr Pro Thr Val Ile Ala Val His Tyr
 51  Leu Asp Gln Thr Glu Gln Trp Glu Lys Phe
 61  Gly Ile Glu Lys Arg Gln Glu Ala Leu Glu
 71  Leu Ile Lys Lys Gly Tyr Thr Gln Gln Leu
 81  Ala Phe Lys Gln Pro Ser Ser Ala Tyr Ala
 91  Ala Phe Asn Asn Arg Pro Pro Ser Thr Trp
101  Leu Thr Ala Tyr Val Val Lys Val Phe Ser
111  Leu Ala Ala Gln Leu Ile Ala Ile Asp Ser
121  His Val Leu Cys Gly Ala Val Lys Trp Leu
131  Ile Leu Glu Lys Gln Lys Pro Asp Gly Val
141  Phe Gln Glu Asp Gly Pro Val Ile His Gln
151  Glu Met Ile Gly Gly Phe Arg Asn Ala Lys
161  Glu Ala Asp Val Ser Leu Thr Ala Phe Val
171  Leu Ile Ala Leu Gln Glu Ala Arg Asp Ile
181  Cys Glu Gly Gln Val Asp Ser Leu Pro Gly
191  Ser Ile Asn Lys Ala Gly Glu Tyr Ile Glu
201  Ala Ser Tyr Met Asn Leu Gln Arg Pro Tyr
211  Thr Val Ala Ile Ala Gly Tyr Ala Leu Ala
221  Leu Met Asn Lys Leu Glu Glu Pro Tyr Leu
231  Gly Lys Phe Leu Asn Thr Ala Lys Asp Arg
241  Asn Arg Trp Glu Glu Pro Asp Gln Gln Leu
251  Tyr Asn Val Glu Ala Thr Ser Tyr Ala Leu
261  Leu Ala Leu Leu Leu Leu Lys Asp Phe Asp
271  Ser Val Pro Pro Val Val Arg Trp Leu Asn
281  Glu Gln Arg Tyr Tyr Gly Gly Gly Tyr Gly
291  Ser Thr Gln Ala Thr Phe Met Val Phe Gln
301  Ala Leu Ala Gln Tyr Gln Thr Asp Val Pro
```

APPENDIX
Sequence Data

*-continued*

```
311  Asp His Asp Leu Asn Met Asp Val Ser Phe

312  His Leu Pro Ser Ser Gly Ser Glu Glu Phe

Seq ID No 38 Oligos for modification of
bacterial vector pBroc413
TAT GAG ATC TCC CGG GGG ATC CTA GCG GCC GCT GCA Seq ID No 39 Oligos for modification of
bacterial vector pBroc413
GCG GCC GCT AGG ATC CCC CGG GAG ATC TCA Seq ID No 40 Peptide for trifunctional linker
Ala Lys Ala Lys Ala Lys Seq ID no 41)
CCACCCGAGCCGGTACCAGATCTA Seq ID no 42
GGTAGATCTGGTACCGGCTCGGCTGG Seq ID No 43:
CGAGCCATATGGGTACCACCCCAGC Seq ID No 44:)
GGTTAGCAGGTACCGGAACC (Seq ID dd)

Seq ID 45 Mutagenic oligo giving addition of
C-terminal cysteine
GGATCTGAAGAGTTCTGCTGAGGATCCTATTAAAGC Seq ID 46 Mutagenic oligo giving addition of
C-terminal cysteine
GCTTTAATAGGATCCTCAGCAGAACTCTTCAGATCC
```

What is claimed is:

1. A nucleic acid sequence encoding at least one autonomously folding polypeptide domain or at least one immunogenic polypeptide having greater than 30 amino acids, wherein the sequence comprises a linear concatamer of at least two non-identical DNA sequences, wherein the non-identical DNA sequences each encode the same amino acid sequence of said autonomously folding polypeptide domain or immunogenic polypeptide that is a ligand of complement receptor type 2 (CR2, CD21), and wherein the concatamer comprises a sequence encoding an oligomer of the autonomously folding polypeptide domain or immunogenic polypeptide in a continuous reading frame.

2. The nucleic acid sequence according to claim 1, wherein a single invariant cysteine codon has been added to a DNA sequence to encode a polypeptide derivative with a unique unpaired cysteine.

3. The nucleic acid sequence according to claim 2, wherein the added cysteine codon is located an the 3' end of the sequence to encode a cysteine at the C-terminus of the polypeptide derivative.

4. The nucleic acid sequence according to claim 1, wherein the concatamer is fused to one or more sequence encoding one or more antigens.

5. The nucleic acid sequence according to claim 1, wherein the concatamer is fused to one or more sequences encoding one or more antigens and a single cysteine codon has been added to or inserted on frame in only one antigen coding sequence.

6. The nucleic acid sequence according to claim 4, wherein the concatamer is fused to one sequence coding one antigen.

7. The nucleic acid sequence according to claim 1, wherein the encoded polypeptide is the complemet C3 fragment Cad, or a sub-fragment thereof.

8. An expression vector comprising a concatamer nucleic acid sequence according to claim 1 and regulatory or other sequences for expression of any oligomeric polypeptide encoded thereby.

9. A host cell comprising an expression vector according to claim 8.

10. A method of making a concatamerised polypeptide, the method comprising expression a concatamer according to claim 1 in a host cell: and
   isolating the expressed product.

11. A method of making a concatamerised polypeptide, the method comprising expression a concatamer according to claim 2:
   isolating an expressed polypeptide having a unique unpaired cysteine and at least one antigen, homo or hereto dimerising the isolated polypeptide through formation of an intermolecular disulphide bond; and
   isolating the dimerised polypeptide.

12. A method of making a concatamerised polypeptide, the method comprising expressing the nucleic acid sequence of claim 2, isolating an expressed polypeptide having a unique unpaired cysteine and at least one antigen; conjugating the unique cysteine residue in the isolated polypeptide to a chemical linker group comprising at least two thiol-reactive functions, and isolating the conjugated polypeptide.

13. A method of making a concatamerised polypeptide, the method comprising expressing the nucleic acid sequence of claim 2; isolating an expressed polypeptide having a unique cysteine residue, and conjugating the unique cysteine residue in the isolated polypeptide through a chemical linkage to an antigen molecule comprising one or more thiol-reactive functions.

14. A method of making an antigen derivative, the method comprising expressing the nucleic acid sequence of claim 2 with a unique unpaired cysteine; separately expressing or preparing an antigen derivative with one or more unpaired cysteines; linking the two entities through an intermolecular disulphide bond, and isolating the product.

15. A composition comprising a pharmaceutically acceptable carrier and the nucleic acid sequence of claim 1.

16. A composition comprising a pharmaceutically acceptable carrier and the expression vector of claim 8.

* * * * *